United States Patent
Yoshimura et al.

(10) Patent No.: US 9,120,862 B2
(45) Date of Patent: Sep. 1, 2015

(54) ANTIBODIES RELATING TO PIVKA-II AND USES THEREOF

(75) Inventors: Toru Yoshimura, Matsudo (JP); Barry Lee Dowell, Mundelein, IL (US); Gangamani S. Beligere, Grayslake, IL (US); Eisaku Yoshida, Kashiwa (JP)

(73) Assignees: ABBOTT LABORATORIES, Abbott Park, IL (US); ABBOTT JAPAN, Matsudo-Shi, Chiba-Ken (JP)

( * ) Notice: Subject to any disclaimer, the term of this patent is extended or adjusted under 35 U.S.C. 154(b) by 586 days.

(21) Appl. No.: 12/843,490

(22) Filed: Jul. 26, 2010

(65) Prior Publication Data
US 2012/0020972 A1   Jan. 26, 2012

(51) Int. Cl.
*G01N 33/53* (2006.01)
*C07K 16/00* (2006.01)
*C07K 16/36* (2006.01)
*C07K 16/44* (2006.01)
*G01N 33/574* (2006.01)

(52) U.S. Cl.
CPC .......... *C07K 16/36* (2013.01); *C07K 16/44* (2013.01); *G01N 33/57438* (2013.01); *C07K 2317/34* (2013.01); *C07K 2317/92* (2013.01)

(58) Field of Classification Search
USPC ........ 424/139.1; 435/7.1, 7.9, 69.6, 331, 346; 530/387.1
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,526,938 A | 7/1985 | Churchill et al. |
| 4,880,078 A | 11/1989 | Inoue et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,241,070 A | 8/1993 | Law |
| 5,290,540 A | 3/1994 | Prince et al. |
| 5,468,646 A | 11/1995 | Mattingly et al. |
| 5,543,524 A | 8/1996 | Mattingly et al. |
| 5,624,821 A | 4/1997 | Winter et al. |
| 5,648,260 A | 7/1997 | Winter et al. |
| 5,679,377 A | 10/1997 | Bernstein et al. |
| 5,705,330 A | 1/1998 | Shah et al. |
| 5,714,350 A | 2/1998 | Co et al. |
| 5,783,699 A | 7/1998 | Mattingly et al. |
| 5,855,913 A | 1/1999 | Hanes et al. |
| 5,874,064 A | 2/1999 | Edwards et al. |
| 5,912,015 A | 6/1999 | Bernstein et al. |
| 5,912,120 A | 6/1999 | Goldstein et al. |
| 5,916,597 A | 6/1999 | Lee et al. |
| 5,934,272 A | 8/1999 | Lloyd et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,350,861 B1 | 2/2002 | Co et al. |
| 6,660,843 B1 | 12/2003 | Feige et al. |
| 7,612,181 B2 | 11/2009 | Wu et al. |
| 2002/0137134 A1 | 9/2002 | Gerngross |
| 2003/0170881 A1 | 9/2003 | Davis et al. |
| 2004/0018577 A1 | 1/2004 | Emerson Campbell et al. |
| 2004/0018590 A1 | 1/2004 | Gerngross et al. |
| 2005/0042664 A1 | 2/2005 | Wu et al. |
| 2005/0054078 A1 | 3/2005 | Miller et al. |
| 2006/0104968 A1 | 5/2006 | Bookbinder et al. |
| 2006/0160164 A1 | 7/2006 | Miller et al. |
| 2010/0233175 A1* | 9/2010 | Yoshimura et al. ........ 424/139.1 |

FOREIGN PATENT DOCUMENTS

| | | |
|---|---|---|
| EP | 0142634 A1 | 5/1985 |
| EP | 0645630 A2 | 3/1995 |
| EP | 1176195 A1 | 1/2002 |
| WO | WO9005144 A1 | 5/1990 |
| WO | WO9105548 A1 | 5/1991 |
| WO | WO9219244 A2 | 11/1992 |
| WO | WO9620698 A2 | 7/1996 |
| WO | WO9732572 A2 | 9/1997 |
| WO | WO9744013 A1 | 11/1997 |
| WO | WO9831346 A1 | 7/1998 |
| WO | WO9915154 A1 | 4/1999 |
| WO | WO9920253 A1 | 4/1999 |
| WO | WO9925044 A1 | 5/1999 |
| WO | WO9954342 A1 | 10/1999 |
| WO | WO9966903 A2 | 12/1999 |
| WO | WO0037504 A2 | 6/2000 |

(Continued)

OTHER PUBLICATIONS

Harlow and Lane (Antibodies, a Laboratory Manual, Cold Spring Harbor Laboratory Press, 1988, p. 53-137, and 141-142).*
Harlow and Lane (Antibodies, a Laboratory Manual, Cold Spring Harbor Laboratory Press, 1988, p. 553-612).*
Dodeigne et al. (Talanta, 2000, 51: 415-439).*
Owens et al. (The Journaofl B Iological Chemistry, 1984, 259 (22): 13800-13805).*
Malhotra et al. (Thrombosis Research 1987, 47; 501-510).*
Adamczyk et al., "Linker-Medicated Modulation of the Cheiluminescent Signal From N10-(3-Sulfopropyl)-N-Sulfonylacridinium-9-carboxamide Tracers," Bioconjugate Chem, 2000, pp. 714-724, vol. 11.
Adamczyk et al., "Modulation of the Chemiluminescent Signal From N10-(3-Sulfopropyl)-N-Sulfonylacridinium-9-carboxamides," Tetrahedron, 1999, pp. 10899-10914, vol. 55.
Adamczyk et al., "Neopentyl 3-Triflyloxypropanesulfaonate Areactive Sulfopropylation Reagent for the Preparation of Chemiluminescent Labels," J Org Chem, 1998, pp. 5636-5639, vol. 63.

(Continued)

Primary Examiner — Yan Xiao
(74) Attorney, Agent, or Firm — Irene M. Reininger

(57) ABSTRACT

The present disclosure relates to antibodies and immunoassay methods for use in the diagnosis, treatment and prevention of hepatocellular carcinoma (HCC), liver cancer and related conditions.

17 Claims, 17 Drawing Sheets

(56) References Cited

FOREIGN PATENT DOCUMENTS

| WO | WO0183525 A2 | 11/2001 |
|---|---|---|
| WO | WO02072636 A2 | 9/2002 |
| WO | WO03016466 A2 | 2/2003 |
| WO | WO03035835 A2 | 5/2003 |
| WO | WO2004067561 A1 | 8/2004 |
| WO | WO2004078140 A2 | 9/2004 |
| WO | WO2005100584 A2 | 10/2005 |
| WO | WO2010104815 A1 | 9/2010 |

OTHER PUBLICATIONS

Adamczyk et al., "Regiodependent Luminescence Quenching of Biotinylated N-Sulfonyl-acridinium-9-carboxamides by Avidin," Organic Letters, 2003, pp. 3779-3782, vol. 5 (21).
Adamczyk et al., "Synthesis of a Chemiluminescent Acridinium Hydroxylamine (AHA) for the Direct Detection of Abasic Sites in DNA," Organic Letters, 1999, pp. 779-781, vol. 1 (5).
Akerstrom et al., "Protein G: A Powerful Tool for Binding and Detection of Monoclonal and Polyclonal Antibodies," Immunology, 1985, 135 (4), pp. 2589-2592.
Altschul S. F., et al., "Gapped BLAST and PSI-BLAST: a new generation of protein database search programs", Nucleic Acids Res., 1997, 25(17), 3389-402.
Annis I., et al., "Disulfide bond formation in peptides," Methods Enzymol, 1997, 289, 198-221.
Ausubel, et al., Current Protocols in Molecular Biology, 1993, Table of Contents.
Bajaj S. P., et al., "Decarboxylation of gamma-carboxyglutamic acid residues in human prothrombin. Stoichiometry of calcium binding to gamma-carboxyglutamic acid in prothrombin," J Biol Chem, 1982, 257 (7), 3726-31.
Bird, et al., "Single-Chain Antigen Binding Proteins," Science, 1988, 242, 423-426.
Buchwald H., et al., "Long-term, continuous intravenous heparin administration by an implantable infusion pump in ambulatory patients with recurrent venous thrombosis," Surgery, 1980, 88, 507-516.
Chothia C., et al., "Canonical Structures for the Hypervariable Regions of Immunoglobulins," J. Mol. Biol, 1987, 196, 901-917.
Chothia C., et al., "Conformations of immunoglobulin hypervariable regions," Nature, 1989, 342, 877-883.
Chothia C., et al., "Structural Repertoire of the Human VH Segments," J. Mol. Biol., 1992, 227, 799-817.
Cleek R. L., et al., "Biodegradable Polymeric Carriers for a bFGF Antibody for Cardiovascular Application," Proc. Intl. Symp. Control. Rel. Bioact. Mater, 1977, 24, 853-854.
Co M. S., et al., "Genetically Engineered Deglycosylation of the Variable Domain Increases the Affinity of an Anti-CD33 Monoclonal Antibody," Molec. Immunol, 1993, 30 (15), 1361-1367.
Durazo, et al., "Des-gamma-carboxyprothrombin, alpha-fetoprotein and AFP-L3 in patients with chronic hepatitis, cirrhosis and hepatocellular carcinoma," J Gastroenterol Hepatol, 2008, 23 (10), 1541-1548.
During M. J., et al., "Controlled Release of Dopamine from a Polymeric Brain Implant: In Vivo Characterization," Ann. Neurol, 1989, 25, 351-356.
Foote J., et al., "Antibody Framework Residues Affecting the Conformation of the Hypervariable Loops," J. Mol. Biol., 1992, 224, 487-489.
Fujiyama S., et al., "Clinical evaluation of plasma abnormal prothrombin (PIVKA-II) in patients with hepatocellular carcinoma," Hepatogastroenterology, 1986, 33 (5), 201-205.
Giege R., et al., "An introduction to the crystallogenesis of biological macromolecules," in: Crystallization of Nucleic Acids & Proteins, a Practical Approach, Ducruix A., 1999, 2, 1-16.
Goldspiel B. R., et al., "Human gene therapy," Clin. Pharm., 1993, 12, 488-505.
Goodson, "Medical Applications of Controlled Release Technology," Langer and Wise, Eds., 1984, 2, 115-138.

Hammerling, et al., "Monoclonal Antibodies and T-Cell Hybridomas: Perspectives and Technical Advances," 1981, 563-681.
Harlow E., et al., "Antibodies: A Laboratory Manual," Table of Contents, 1988, Cold Spring Harbor Laboratory Press.
Herai, et al., ""Evaluation of PIVKA-II Assay by Chemiluminescent Enzyme immunoassay and its Clinical Usefulness in Hepatocellular Carcinoma,"" Japanese J Clinical Laboratory Automation, 2007, 32 (2), 205-210.
Higgins D. G., et al., "Fast and sensitive multiple sequence alignments on a microcomputer," CABIOS Comm., 1989, 5 (2), 151-153.
Holliger Philipp, et al, "Diabodies: Small bivalent and bispecific antibody fragments", Proc. Natl. Acad. Sci., 1993, 90, Biophysics, 6444-6448.
Howard III, M. A., et al., "Intracerebral drug delivery in rats with lesion-induced memory deficits," J. Neurosurg., 1989, 71, 105-112.
Huston, et al., "Protein Engineering of Antibody Binding Sites: Recovery of Specific Activity in an Anti-Digoxin Single-Chain Fv Analogue Produced in *Escherichia coli*," PNAS USA, 1988, vol. 85 (16), pp. 5879-5883.
Jefferis R., et al., "Glycosylation of recombinant antibody therapeutics," Biotechnol Prog, 2005, 21 (1), 11-16.
Johnsson B., et al., "Comparison of Methods for Immobilizatoin to Carboxymethyl Dextran Sensor Surfaces by Analysis of the Specific Activity of Monoclonal Antibodies," J. Molecular Recog, 1995, 8, 125-131.
Johnsson B., et al., "Immobilization of proteins to a carboxymethyldextran-modified gold surface for biospecific interaction analysis in surface plasmon resonance sensors," Anal. Biochem, 1991, 198, 268-277.
Joliot A., et al., "Antennapedia homeobox peptide regulates neural morphogenesis," PNAS USA, 1991, 88, 1864-1868.
Jonsson, et al, "Real-Time Biospecific Interaction Analysis Using Surface Plasmon Resonance and a Sensor Chip Technology", Bio-Technics, 1991, 11 (5), 620-627.
Jonsson U., et al., "Introducing a biosensor based technology for real-time biospecific interaction analysis", Ann. Biol. Clin., (1993), 51, 19-26.
Kabat E. A., et al., "Attempts to Locate Complementarity-Determining Residues in the variable Positions of Light and Heavy Chains," Ann. NY Acad. Sci,1971, 190, 382-391.
Kabat E. A., et al., "Sequences of Proteins of Immunological Interest," NIH Publ. #91, 1991, 5, Table of Contents.
Kabat Elvin A., et al., "Sequences of Proteins of Immunological Interest", 1987.
Kaufman R. J., et al., "Amplification and Expression of Sequences Cotransfected with a Modular Dihydrofolate Reductase Complementary DNA Gene," J. Mol. Biol., 1982, 159, 601-621.
Kipriyanov S. M., et al., "Recombinant Single-Chain Fv Fragments Carrying C-Terminal Cysteine Residues: Production of Bivlent and Biotinylated Miniantibodies," Molecular Immunology, 1994, 31, 1047-1058.
Kipriyanov S. M., et al., "Single-chain Antibody Streptavidin Fusions: Tetrameric Bifunctional scFv-Complexes with Biotin Binding Activity and Enhanced Affinity to Antigen," Human Antibodies and Hybridomas, 1995, 6, 93-101.
Kontermann D., ed., Antibody Engineering, Table of Contents., 2001.
Koteish Ayman, et al, "Screening for Hepatocellular Carcinoma", Vasc Intery Radio, 2002, 13, Screening for Hepotocellur Carinoma, 182-190.
Kriegler M., Gene Transfer and Expression: A Laboratory Manual, Stockton Press, Table of Contents, 1990.
Kronvall G., et al, "A surface component in group A, C, and G *streptococci* with non-immune reactivity for immunoglobulin G", Journal of Immunology, 1973, vol. 111 (5), pp. 1401-1405.
Lam X. M., et al., "Microencapsulation of Recombinant Humanized Monoclonal Antibody for Local Delivery," Procelna Symp. Control. Rel. Bioact. Mater., 1997, 24, 759-760.
Langer R., et al., "Chemical and Physical Structure of Polymers as Carriers for Controlled Release of Bioactive Agents: A Review," J of Macromolecular Science, Part C: Polymer Reviews, 1983, 23, 61-126.
Langer R., "New Methods of Drug Delivery," Science, 1990, 249, 1527-1533.
Langer Robert S., et al, "Medical Applications of Controlled Relese", Classes of Systems, 1984, 1, CRC Press Inc.

(56) References Cited

OTHER PUBLICATIONS

Levy, et al., "Inhibition of Calcification of Bioprosthetic Heart Valves by Local Controlled-Release Diphosphonate," Science, 1985, 228, 190-192.
Liebman H. A., et al., "Des-gamma-carboxy (abnormal) prothrombin as a serum marker of primary hepatocellular carcinoma," N Engl J Med, 1984, 310 (22), 1427-1431.
MacCallum, et al., "Antibody-antigen Interactions: Contact Analysis and Binding Site Topography," J. Mol. Biol., 1996, 262 (5), 732-745.
Marreo Jorge A., et al, "Des-Gamma Carboxyprothrombin Can Differentiate Hepatocellular Carcinoma From Nonmalignant Chronic Liver Disease in American Patients", Hepatology, 2003, 37 (5), 1114-1121.
Mattingly et al., "Chemiluminescent N-Sulfonylacridinium-9-Carboxamides and Their Application in Clinical Assays," Luminescence Biotechnology: Instruments and Applications (CRC Press: Boca Raton 2000), 2002, pp. 77-105.
Mattingly Phillip G., "Chemiluminescent 10-Methyl-Acridinium-9(N-Sulphonylcarboxamide) Salts. Synthesis and Kinetics of Light Emission," Journal of Bioluminescence and Chemiluminescence, 1991, pp. 107-114, vol. 6.
McCapra, "Chemiluminescence Involving Peroxide Decompositions," Photochemistry and Photobiology, 1965, pp. 1111-1121, vol. 4.
Morgan R. A., et al., "Human Gene Therapy," Ann. Rev. Biochem., 1993, 62, 191-217.
Mulligan R. C., "The Basic Science of Gene Therapy," Science, 1993, 260, 926-932.
Naraki T., et al., "gamma-Carboxyglutamic acid content of hepatocellular carcinoma-associated des-gamma-carboxy prothrombin," Biochim Biophys Acta, 2002, 1586 (3), 287-298.
Needleman S. B., et al., "A General Method Applicable to the Search for Similarities in the Amino Acid Sequence of Two Proteins," J Mol Biol, 1970, 48, 443-453.
Ning S., et al., "Intratumoral radioimmunotherapy of a human colon cancer xenograft using a sustained-release gel," Radiotherapy & Oncology, 1996, 39, 179-189.
Padlan E. A., et al., "Identification of specificity-determining residues in antibodies", FASEBJ, 1995, 9, 133-139.
Pearson W. R., et al., "Improved tools for biological sequence comparison," PNAS USA, 1988, 85, 2444-2448.
Poljak R. J., et al., "Production and Structure of Diabodies," Structure, 1994, 2, 1121-1123.
Quinn Frank A., "36 Bulk Reagent Random-Access Analyzer: ARCHITECT i2000," The Immunoassay Handbook, 2001, 2, Wild D., Ed., 363-367.
Razavi, "Stable and versatile active acridinium esters I," Luminescence, 2000, pp. 239-244, vol. 15.
Razavi, "Stable and versatile active acridinium esters II," Luminescence, 2000, pp. 245-249, vol. 15.
Remington, "Pharmaceutical Sciences and Introduction to Pharmaceutical Dosage Forms," 1995, 19, Mack Pub. Co.
Robinson, "Gene therapy—proceeding from laboratory to clinic," TIBTECH, 1993, 11 (5), 155-215.
Sakaguchi, et. al., "Generation of high-affinity antibody against T cell-dependent antigen in the Ganp gene-transgenic mouse," J Immunol, 2005, 174 (8), 4485-4494.
Sambrook J., et al., "Molecular Cloning—A Laboratory Manual," 1989, 2, Cold Spring Harbor Laboratory Press, Table of Contents.
Saudek C. D., et al., "A Preliminary Trail of the Programmable Implantable Medication System for Insulin Delivery," New Engl. J. Med., 1989, 321 (9), 574-579.
Sefton M. V., "Implantable Pumps," Critical Reviews in Biomedical Engineering, 1987, 14 (3), 201-240.
Shields R. L., et al., "Lack of Fucose on Human IgG1 N-Linked Oligosaccharide Improves Binding to Human Fc[gamma]RIII and Antibody-dependent Cellular Toxicity," J. Biol. Chem., 2002, 277 (30), 26733-26740.
Smith, et al.,"Comparison of Biosequences", Adv. Appl. Math, 1981, 2, 482-489.
Smolen Victor F., et al , "Controlled Drug Bioavailability", 1984, 1.
Song Y. K., et al., "Antibody Mediated Lung Targeting of Long-Circulating Emulsions," PDA J. Pharm. Sci. & Tech, 1995, 50, 372-397.
Suzuki M., et al., "Des-gamma-carboxy prothrombin is a potential autologous growth factor for hepatocellular carcinoma," J Biol Chem, 2005, 280 (8), 6409-15.
Tetin S. Y., et al., "Interactions of two monoclonal antibodies with BNP: high resolution epitope mapping using fluorescence correlation spectroscopy," Biochemistry, 2006, 45 (47), 14155-65.
Tolstoshev P., "Gene therapy, concepts, current trials and future directions," Annu Rev Pharmacol Toxicol, 1993, 33, 573-96.
Umana P., et al., "Engineered glycoforms of an antieuro-blastoma IgG1 with optimized antibody-dependent cellular cytotoxic activity," Nature Biotech., 1999, 17, 176-180.
Urlaub, et al., "Isolation of Chinese Hamster Cell Mutants Deficient in Dihydrofolate Reductase Activity," PNAS USA, 1980, 77, 4216-4220.
Wallick S. C., et al., "Glycosylation of a VH Residue of a Monoclonal Antibody Against a (1-46) Dextran Increases Its Affinity for Antigen," J. Exp. Med., 1988, 168, 1099-1109.
Ward E. S., et al., "Binding activities of a repertoire of single immunoglobulin variable domains secreted from *Escherichia coli*," Nature, 1989, 341, 544-546.
Wright A., et al., "Antibody variable region glycosylation: position effects on antigen binding and carbohydrate structure," The EMBO J., 1991, 10 (10), 2717-2723.
Wu G. Y., et al., "Delivery systems for gene therapy," Biotherapy, 1991, 3, 87-95.
Wu G.Y., et al.,"Receptor-mediated in Vitro Gene Transformation by a Soluble DNA Carrier System," J. Biol. Chem., 1987, 262, 4429-4432.
Yamaguchi I., et al., "Development of des-gamma-carboxy prothrombin (DCP) measuring reagent using the LiBASys clinical analyzer," Clin Chem Lab Med, 2008, 46 (3), 411-416.
Yuen M. F., et al., "Serological markers of liver cancer," Best Pract Res Clin Gastroenterol, 2005, 19 (1), 91-99.
Belle M., et al., "Production of a New Monoclonal Antibody Specific to Human Des-Gamma-Carboxyprothrombin in the Presence of Calcium Ions. Application to the Development of a Sensitive ELISA-Test," Journal of Immunoassay, 1995, vol. 16 (2), pp. 213-229.
Grosley B.M., et al., "Specific Measurement of Hypocarboxylated Prothrombin in Plasma or Serum and Application to the Diagnosis of Hepatocellular Carcinoma," Journal of Laboratory and Clinical Medicine, 1996, vol. 127 (6), pp. 553-564.
International Search Report and Written Opinion for Application No. PCT/US2011/043316, mailed on Dec. 13, 2011, 16 pages.
Nakao A., et al., "Clinical Application of a New Monoclonal Antibody (19B7) against PIVKA-II in the Diagnosis of Hepatocellular Carcinoma and Pancreatobiliary Malignancies," American Journal of Gastroenterology, 1997, vol. 92 (6), pp. 1031-1034.
Owens J., et al., "Monoclonal Antibodies against Human Abnormal Prothrombin Specific for the Calciam free," Journal of Biological Chemistry, 1984, vol. 259 (22), pp. 13800-13805.
Sekiya C., et al., "Characterstics of PIVKA Found in Hepatocellular Carcinoma, Investigation Using Monoclonal Antibodies MU-3 and 19B7," International Hepatology Communications, 1994, vol. 2 (5), pp. 277-284.
Sugimoto H., et al., "Des-Gamma-Carboxy Prothrombin (DCP) Ratio, a Novel Parameter Measured by Monoclonal Antibodies MU-3 and 19B7, as a New Prognostic Indicator for Hepatocellular Carcinoma," Liver International, 2003, vol. 23 (1), pp. 38-44.
Uehara S., et al., "Distribution of the Heterogeneity of Des-Gamma-Carboxyprothrombin in Patients with Hepatocellular Carcinoma," Journal of Gastroenterology and Hepatology, 2005, vol. 20 (10), pp. 1545-1552.

* cited by examiner

| PIVKAII Gla domain (13-27) analogs | Apparent Diffusion Coefficient (D) um^2/sec |
|---|---|
| Positive Control | 174±10 |
| Negative Control | 47±4 |
| Protein C peptide | 53±5 |
| Protein S peptide | 50±5 |
| Protein Z peptide | 51±5 |
| Factor VII peptide | 49±5 |
| Factor IX peptide | 48±5 |
| Factor X peptide | 52±5 |

ANTIBODIES RELATING TO PIVKA-II AND USES THEREOF

SEQUENCE LISTING

The instant application contains a Sequence Listing which has been submitted in ASCII format via EFS-Web in accordance with 37 C.F.R. §1.821-1.825 and is hereby incorporated by reference in its entirety. Said ASCII copy, created Jan. 2, 2013, is named 10281US0.txt and is 8,849 bytes in size.

FIELD OF THE INVENTION

The present disclosure relates to antibodies and immunoassay methods that may be used, for example, in the diagnosis, treatment and prevention of hepatocellular carcinoma (HCC), liver cancer and related conditions.

BACKGROUND OF THE INVENTION

The protein Prothrombin II, also known as Factor II, undergoes a post-synthetic modification in the presence of Vitamin K wherein ten glutamate (GLA) residues in the GLA-domain are carboxylated to g-carboxy glutamic acid. The carboxylation process is aberrant and incomplete in the diseased state and the process by which prothrombin is converted to PIVKA-II (Protein Induced by Vitamin K Absence). PIVKA-II is a large glycoprotein having a 72 KDa molecular mass and known to be elevated in the case of HCC patients (Liebman et al., The *New England Journal of Medicine* (1984), 310 (22), pages 1427-1431; Fujiyama et al., Hepatogastroenterology (1986), 33, pages 201-205; Marreo et al., *Hepatology* (2003), 37, pages 1114-1121). At present, available methods for detecting HCC or liver cancer by use of biomarkers are ineffective (Koteish et al., *J. Vasc. Interv. Radiol.* (2002), 13, pages 185-190; Yuen et al., *Best Practice & Research Clinical Gastroenterology* (2005), 19, pages 91-99; see also Herai et al., *Japanese Journal of Clinical Laboratory Automation* (2007), 32(2), pages 205-210; Durazo et al., *Journal of Gastroenterology and Hepatology* (2008), 23, pages 1541-1548; Yamaguchi et al., *Clin. Chem. Lab. Med.* (2008), 46(3), pages 411-416). Further, only a few monoclonal antibodies are known which have the binding specificity required to be useful in immunoassays that effectively detect such conditions or to treat such conditions (Naraki et al., Biochemica et Biophysica Acta (2002) 1586, pages 287-298). Thus, a great need exists in oncology for the development of antibodies that can be used effectively for detecting HCC or liver cancer.

SUMMARY OF THE INVENTION

In one aspect, the present disclosure provides a hybridoma cell line designated by American Type Culture Collection (ATCC) deposit designation PTA-10541. The present disclosure also provides a monoclonal antibody produced by the hybridoma cell line designated by American Type Culture Collection (ATCC) deposit designation PTA-10541.

In another aspect, the present disclosure provides an isolated binding protein comprising an antigen binding portion that binds to amino acids 1-13 of Prothrombin Induced Vitamin K Antagonist II (PIVKA-II). In an exemplary embodiment, the isolated binding protein has a binding dissociation constant of about $4.0 \times 10^{-9}$ M or lower.

In another aspect, the present disclosure provides an isolated nucleic acid molecule encoding a binding protein that binds to PIVKA-II, wherein the binding protein has a variable heavy chain region, the amino acid sequence of the variable heavy chain region having at least 70% sequence identity with the amino acid sequence of the monoclonal antibody produced by the hybridoma cell line designated by American Type Culture Collection (ATCC) deposit designation PTA-10541. With reference to the binding protein, the isolated nucleic acid molecule may encode a binding protein having an antigen binding portion binds to amino acids 1-13 of PIVKA-II. The isolated nucleic acid molecule may be provided in a vector. An isolated host cell may comprise such a vector.

In another aspect, the present disclosure provides a purified amino acid sequence having at least 70% sequence identity with the amino acid sequence of the monoclonal antibody produced by the hybridoma cell line designated by American Type Culture Collection (ATCC) deposit designation PTA-10541.

In another aspect, the present disclosure provides a method of producing a binding protein capable of binding to PIVKA-II, the method comprising the steps of: a) constructing a vector comprising the nucleic acid molecule of described above operably linked to a regulatory element; b) transforming the resulting vector into a host cell; c) culturing the host cell for a time and under conditions sufficient to produce the binding protein. The disclosure further provides an isolated binding protein produced according to such a method.

In another aspect, the present disclosure provides a method for detecting PIVKA-II antigen in a test sample, the method comprising the steps of: a) contacting the test sample with an antibody having an antigen binding portion that binds to amino acids 1-13 of PIVKA-II and for a time and under conditions sufficient for the formation of antibody-antigen complexes; and b) detecting the presence of the antibody-antigen complexes, wherein the presence of the antibody-antigen complexes indicates the presence of PIVKA-II in the test sample. The antibody can be a monoclonal antibody produced by a hybridoma cell line having ATCC deposit designation PTA-10541.

In the above method for detecting as PIVKA-II in a test sample, and in any of the methods described herein, the test sample can be whole blood, serum or plasma. In the methods, an antibody can be labeled with a detectable label and the method can include measuring the signal generated by or emitted from the detectable label and detecting the PIVKA-II antigen in the test sample. The detectable label can be a radioactive label, an enzymatic label, a chemiluminescent label, a fluorescence label, a thermometric label, and an immuno-polymerase chain reaction label. The detectable label can be, for example, an acridinium compound. When the detectable label is an acridinium compound, the method may further comprise: a) generating or providing a source of hydrogen peroxide to the antibody-antigen complexes; b) adding a basic solution to the mixture of step (a); and c) measuring the light signal generated or emitted in step (b) and detecting PIVKA-II in the sample.

In another aspect, the present disclosure provides a method of detecting PIVKA-II antigen in a test sample comprising the steps of: a) contacting the test sample with a first antibody having an antigen binding portion that binds to amino acids 13-27 of PIVKA-II, for a time and under conditions sufficient for the formation of first antibody-antigen complexes; b) adding a second antibody to the first antibody/antigen complexes, wherein the second antibody has an antigen binding portion that binds to amino acids 1-13 of PIVKA-II and is conjugated to a detectable label, for a time and under conditions sufficient to form first antibody/antigen/second antibody complexes; and c) measuring the signal generated by or emitted from the detectable label and detecting the PIVKA-II antigen in the test sample. The first antibody can be a monoclonal antibody produced by a hybridoma cell line having ATCC deposit designation PTA-9638. The second antibody can be a monoclonal antibody produced by a hybridoma cell line having ATCC deposit designation PTA-10541.

In another aspect, the present disclosure provides a method of detecting PIVKA-II antigen in a test sample comprising the steps of: a) contacting the test sample with 1) a PIVKA-II reference antigen, wherein the reference antigen is attached to a detectable label capable of generating a detectable signal and 2) an antibody to PIKVA-II antigen, for a time and under conditions sufficient to form PIVKA-II reference antigen/antibody complexes; b) detecting a signal generated by the detectable label, wherein the amount of PIVKA-II antigen detected in the test sample is inversely proportional to the amount of PIVKA-II reference antigen bound to the antibody. In the method, the antibody can comprise an antigen-binding domain that binds to amino acids 1-13 of PIVKA-II, and can be for example a monoclonal antibody produced by a hybridoma cell line having ATCC deposit designation PTA-10541.

In another aspect, the present disclosure provides a method of producing a hybridoma cell line that expresses a binding protein comprising an antigen-binding domain that binds to amino acids 1-13 of PIVKA-II, comprising the steps of: a) immunizing a GANP mouse with an antigen comprising amino acids 1-17 of PIVKA-II for a time and under conditions sufficient for the mouse to produce antibodies against the antigen; b) harvesting and purifying eight cells from the spleen of the mouse; c) fusing the spleen cells with myeloma cells in order to produce hybridomas; and d) selecting a hybridoma cell line which expresses the binding protein comprising an antigen-binding domain which binds to amino acids 1-13 of PIVKA-II. In the method, the hybridoma cell line can be the cell line having ATCC deposit designation PTA-10541.

In another aspect, the present disclosure provides a pharmaceutical composition comprising a binding protein comprising an antigen-binding domain that binds to amino acids 1-13 of PIVKA-II, and a pharmaceutically acceptable carrier. In the pharmaceutical composition, the binding protein may comprise a monoclonal antibody produced by a hybridoma cell line having ATCC deposit designation PTA-10541.

In another aspect, the present disclosure provides a method of diagnosing HCC or liver cancer in a patient suspected of having HCC or liver cancer comprising the steps of: a) isolating a biological sample from the patient; b) contacting the biological sample with an antibody comprising an antigen binding portion that binds to amino acids 1-13 of PIVKA-II antigen for a time and under conditions sufficient for formation of PIVKA-II antigen/antibody complexes; and c) detecting presence of the PIVKA-II antigen/antibody complexes; d) dissociating the PIVKA-II antigen present in the complexes from the antibody present in the complexes; and e) measuring the amount of dissociated PIVKA-II antigen, wherein an amount of dissociated PIVKA-II antigen greater than a predetermined level indicates a diagnosis of HCC or liver cancer in the patient. In the method, the predetermined level can be for example about 40 mAU/mL. In the method, the antibody can be a monoclonal antibody produced by the hybridoma cell line having ATCC deposit designation PTA-10541.

In another aspect, the present disclosure provides a method of diagnosing HCC or liver cancer in a patient suspected of having HCC or liver cancer, comprising the steps of: a) isolating a biological sample from the patient; b) contacting the biological sample with a first antibody having an antigen binding domain that binds to amino acids 13-27 of PIVKA-II antigen for a time and under conditions sufficient for the formation of PIVKA-II antigen/antibody complexes; c) adding a conjugate to the resulting PIVKA-II antigen/antibody complexes for a time and under conditions sufficient to allow the conjugate to bind to the bound PIVKA-II antigen, wherein the conjugate comprises a second antibody having an antigen binding domain that binds to amino acids 1-13 of PIVKA-II and is attached to a detectable label capable of generating a detectable signal; d) detecting the presence of PIVKA-II antigen which may be present in the biological sample by detecting a signal generated by the detectable label; and e) measuring the amount of PIVKA-II antigen present in the test sample by measuring the intensity of the signal, wherein an amount of PIVKA-II antigen greater than a predetermined level is indicative of the presence of HCC or liver cancer in the patient. In the method, the predetermined level can be about 40 mAU/mL. In the method, the first antibody can be a monoclonal antibody produced by the hybridoma cell line having ATCC deposit designation PTA-9638 (mAb 3C10). The second antibody can be a monoclonal antibody produced by the hybridoma cell line having ATCC deposit designation PTA-10541. The first antibody can be immobilized on a solid phase either before or after the formation of the first antibody-antigen complexes.

In another aspect, the present disclosure provides a kit for detecting and/or quantifying an amount of PIVKA-II in a test sample, the kit comprising a container containing a monoclonal antibody produced by the hybridoma cell line having ATCC deposit designation PTA-10541, or a binding protein having an antigen binding domain that binds to amino acids 1-13 of PIVKA-II. The kit may further comprise a container containing a binding protein having an antigen binding domain that binds to amino acids 13-27 of PIVKA-II.

In another aspect, the present disclosure provides a kit for detecting and/or quantifying an amount of PIVKA-II in a test sample, the kit comprising: a detection reagent comprising an antibody having an antigen binding portion that binds to amino acids 1-13 of PIVKA-II; and instructions for detecting and/or quantifying the amount of PIVKA-II in the test sample. In the kit, the antibody may be a monoclonal antibody produced by the hybridoma cell line designated by American Type Culture Collection (ATCC) deposit designation PTA-10541. In the kit, a detectable label can be attached to the antibody, wherein the detectable label is capable of generating a detectable signal. In the above kit, and in any of the above methods, when a detectable label is used, the detectable label can be selected from the group consisting of a radioactive label, an enzymatic label, a chemiluminescent label, a fluorescence label, a thermometric label, and an immunopolymerase chain reaction label, and in particular may be an acridinium compound. The acridinium compound may be an acridinium-9-carboxamide having a structure according to formula I:

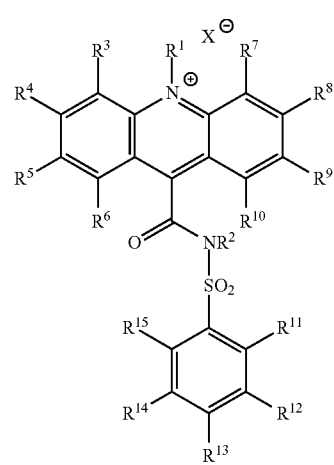

wherein R1 and R2 are each independently selected from the group consisting of: alkyl, alkenyl, alkynyl, aryl or aralkyl, sulfoalkyl, carboxyalkyl and oxoalkyl, and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Alternatively, the acridinium compound may be an acridinium-9-carboxylate aryl ester having a structure according to formula II:

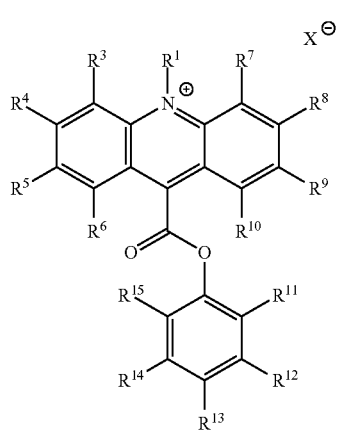

II wherein R1 is an alkyl, alkenyl, alkynyl, aryl or aralkyl, sulfoalkyl, carboxyalkyl and oxoalkyl; and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion. In the above kit, when an acridinium compound is included as the detectable label, the kit may further comprise a basic solution. The basic solution can be a solution having a pH of at least about 10. The kit may also include a hydrogen peroxide source, such as a buffer or a solution containing hydrogen peroxide. The hydrogen peroxide source may comprise a hydrogen peroxide generating enzyme, such as a hydrogen peroxide generating enzyme selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase,

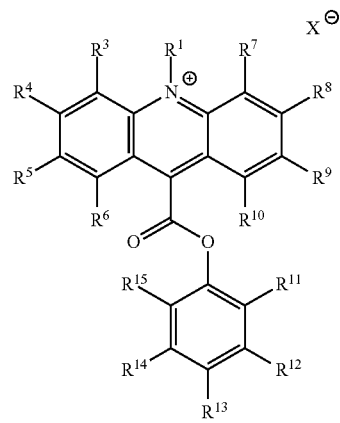

II ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof. When the detectable label is an acridinium compound, the kit may further comprise a basic solution. The basic solution can be for example a solution having a pH of at least about 10. The kit may further comprise a hydrogen peroxide source. The hydrogen peroxide source can comprise a buffer or a solution containing hydrogen peroxide. The hydrogen peroxide source can comprise a hydrogen peroxide generating enzyme. The hydrogen peroxide generating enzyme can be selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

In another aspect, the present disclosure provides a kit for detecting and/or quantifying an amount of PIVKA-II in a test sample, comprising a first isolated binding protein comprising an antigen binding portion that binds to amino acids 13-27 of PIVKA-II, and a second isolated binding protein comprising an antigen binding portion that binds to amino acids 1-13 of PIVKA-II. The first and second isolated binding proteins can be monoclonal antibodies. The first monoclonal antibody can be an antibody produced by the hybridoma cell line designated by American Type Culture Collection (ATCC) deposit designation PTA-9638, and the second monoclonal antibody can be an antibody produced by the hybridoma cell line designated by American Type Culture Collection (ATCC) deposit PTA-10541.

In another aspect, the present disclosure provides a method for determining an amount of PIVKA-II in a sample comprising use of at least two different binding proteins wherein each binding protein comprises an antigen binding portion that specifically binds to a subset of amino acids 1-33 of PIVKA-II, wherein the antigen binding portion of each binding protein binds to a different subset of amino acids 1-33 of PIVKA-II. The binding proteins can be monoclonal antibodies. A first monoclonal antibody can have an antigen binding portion that binds to PIVKA-II, and a second monoclonal antibody can have an antigen binding portion that binds to PIVKA-II and an antigen binding portion that binds to at least a subset of amino acids 1-33 of prothrombin. The first monoclonal antibody can have for example an antigen binding portion that binds to amino acids 13-27 of PIVKA-II, and the second monoclonal antibody can have for example an antigen binding portion that binds to amino acids 1-13 of PIVKA-II. The first monoclonal antibody can be for example an antibody produced by the hybridoma cell line designated by American Type Culture Collection (ATCC) deposit designation PTA-9638, and the second monoclonal antibody can be an antibody produced by the hybridoma cell line designated by American Type Culture Collection (ATCC) deposit PTA-10541.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

A. Introduction and Definitions

Figure 1:
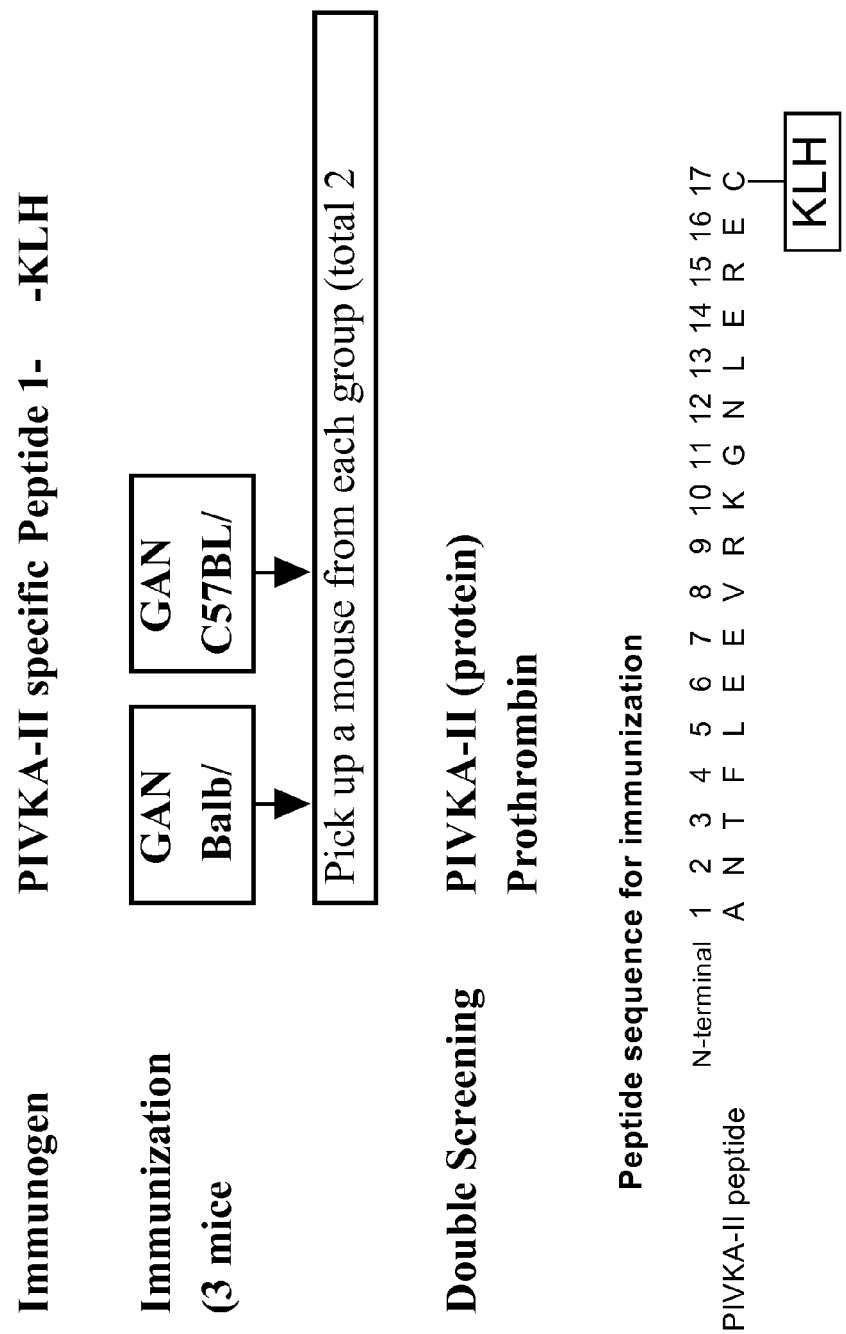
FIG. 1 is a schematic diagram showing use of Peptide KLH (SEQ ID NO: 18) to immunize three germinal center-associated DNA primase (GANP) transgenic Balb/c mice and three GANP transgenic C57BL/6 mice.

The GLA domain of the PIVKA-II protein consists of amino acids 1-46 (or 44-88 of prothrombin sequence), including ten GLA amino acids. The PIVKA protein exists in multiple forms that vary as to the position and number of decarboxylated GLA's. Currently available immunoassays for PIVKA-II detect only a portion of the protein, primarily the sequence of amino acids 17-23 of the cyclic disulfide bond, and surrounding sequences, i.e., amino acids 13-27. As a result, GLA's outside of amino acids 17-23 including decarboxylated GLA's are not detected. The new antibodies and methods disclosed herein provide a way to detect amino acids 1-17 of PIVKA, and the decarboxylated residues in the region of amino acids 17-23. This can be achieved, for example, by using a first anti-PIVKA antibody having an antigen binding portion that binds to amino acids 13-27 of PIVKA-II, and a second anti-PIVKA antibody having an antigen binding portion that binds to amino acids 1-13 of PIVKA-II. The second antibody can strongly react with decarboxylated amino acid residues of PIVKA, and moderately react with the carboxylated (normal) amino acid residues. Use of both antibodies in an assay can detect both PIVKA 13-27 and PIKVA 1-27 with a high level of specificity, and thus generates a stronger signal than that generated by detection of PIKVA 13-27 alone.

The present disclosure thus provides a binding protein and, in particular, a monoclonal antibody, hereinafter "6H6" that binds to one or more epitopes of PIVKA-II, with a $K_d$ for the PIVKA-II peptide of 37±4 nM or less, and preferably in a range of $1\times10^{-9}$ M or greater, preferably about $1\times10^{-10}$ M or greater. In particular, the binding protein or antibody of the present disclosure has a dissociation constant (KO to the 1-13 amino acid region of PIVKA-II of about $1\times10^{-9}$ M or greater, preferably about $1\times10^{-10}$ M or greater. The antibody is thus capable of specifically recognizing and binding to PIVKA-II. Once it is bound to PIVKA-II, it is not replaced by prothrombin. In a situation in which the antibody is exposed to PIVKA-II and prothrombin at the same time, it is noteworthy that the 6H6 antibody of the present disclosure has about 10 to about 1000 times lower affinity to prothrombin than to PIVKA-II. The subject invention also includes isolated nucleotide sequences (and fragments thereof) encoding the variable light and heavy chains of the antibodies of the present disclosure as well as those nucleotide sequences (or fragments thereof) having sequences comprising, corresponding to, identical to, hybridizable to, or complementary to, at least about 70% (e.g., 70% 71%, 72%, 73%, 74%, 75%, 76%, 77%, 78% or 79%), preferably at least about 80% (e.g., 80%, 81%, 82%, 83%, 84%, 85%, 86%, 87%, 88% or 89%), and more preferably at least about 90% (e.g., 91%, 92%, 93%, 94%, 95%, 96%, 97%, 98%, 99% or 100%) identity to these encoding nucleotide sequences. (All integers (and portions thereof) between and including 70% and 100% are considered to be within the scope of the present disclosure with respect to percent identity.) Such sequences may be derived from any source (e.g., either isolated from a natural source, produced via a semi-synthetic route, or synthesized de novo). In particular, such sequences may be isolated or derived from sources other than described in the examples (e.g., bacteria, fungus, algae, mouse or human). In addition to the nucleotide sequences described above, the present disclosure also includes amino acid sequences of the variable light and heavy chains of the antibodies described herein (or fragments of these amino acid sequences).

Further, the present disclosure also includes amino acid sequences (or fragments thereof) comprising, corresponding to, identical to, or complementary to at least about 70% (e.g., 70%, 71%, 72%, 73%, 74%, 75%, 76%, 77%, 78% or 79%), preferably at least about 80% (e.g., 80% 81%, 82%, 83%, 84%, 85%, 86%, 87%, 88% or 89%), and more preferably at least about 90% identity (e.g., 90%, 91%, 92%, 93%, 94%, 95%, 96%, 97%, 98%, 99% or 100%), to the amino acid sequences of the proteins of the present disclosure. (Again, all integers (and portions thereof) between and including 70% and 100% (as recited in connection with the nucleotide sequence identities noted above) are also considered to be within the scope of the present disclosure with respect to percent identity.) For purposes of the present disclosure, a "fragment" of a nucleotide sequence is defined as a contiguous sequence of approximately at least 6, preferably at least about 8, more preferably at least about 10 nucleotides, and even more preferably at least about 15 nucleotides corresponding to a region of the specified nucleotide sequence. The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield 15 the number of matched positions, dividing the number of such positions by the total number of positions in the segment being compared and multiplying the result by 100. Optimal alignment of sequences may be conducted by the algorithm of Smith & Waterman, *App. Math.* 2:482 (1981), by the algorithm of Needleman & Wunsch, *J. Mol. Biol.* 48:443 (1970), by the method of Pearson & Lipman, *Proc. Natl. Acad. Sci.* (USA) 85:2444 (1988) and by computer programs which implement the relevant algorithms (e.g., Clustal Macaw Pileup (http://cmgm.stanford.edu/biochem218/11Multiple.pdf; Higgins et al., CABIOS. 5L151-153 (1989)), FASTDB (Intelligenetics), BLAST (National Center for Biomedical Information; Altschul et al., *Nucleic Acids Research* 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present disclosure, "complementarity" is defined as the degree of relatedness between two DNA segments. It is determined by measuring the ability of the sense strand of one DNA segment to hybridize with the antisense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments. "Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art. "Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The term "biological activity" as used herein refers to all inherent biological properties of PIVKA-II. Such properties include, for example, the ability to bind to the antibodies described herein. "Functional equivalent" as used herein, refers to a protein (e.g., an antibody) having the same characteristics (e.g., binding affinity) of the antibodies of the present disclosure.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric. The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The terms "binding", "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., one or more epitopes of PIVKA-II). It has been shown that the antigen-binding function of an antibody can be performed by one or more fragments of a full-length antibody. Such antibody embodiments may also be bispecific, dual specific, or multispecific, specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., International App. Publication No. WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., *Antibody Engineering* (2001) Springer-Verlag. New York. 790 pp. (ISBN 3-540-41354-5).

The term "antibody construct" as used herein refers to a polypeptide comprising one or more the antigen binding portions of the present disclosure linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Human IgG heavy chain and light chain constant domain amino acid sequences are known in the art. Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab') 2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds at least one epitope of PIVKA-II with which the antibodies of the present disclosure are reactive and is substantially free of antibodies that specifically bind antigens or epitopes other than those present within PIVKA-II.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and Kabat, E. A., et al. (1991) *Sequences of Proteins of Immunological Interest*, Fifth Edition, U.S. Department of Health and Human Services, NIH Publication No. 91-3242).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions.

The term "CDR set" as used herein refers to a group of three CDRs that occur in a single variable region capable of binding the antigen. The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, *J. Mol. Biol.* 196:901-917 (1987) and Chothia et al., *Nature* 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (*FASEB J.* 9:133-139 (1995)) and MacCallum (LT *Mol Biol* 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (*J. Mol. Biol.* 196:901-907 (1987); Chothia et al., *J. Mol. Biol.* 227: 799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or 0-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework. As used herein, "Vernier" zone refers to a subset of framework residues that may adjust CDR structure and fine-tune the fit to antigen as described by Foote and Winter (1992, *J. Mol. Biol.* 224:487-499, which is incorporated herein by reference). Vernier zone residues form a layer underlying the CDRs and may impact on the structure of CDRs and the affinity of the antibody.

The term "activity" includes activities such as the binding specificity/affinity of an antibody for an antigen, for example, the antigen or antigens which the antibodies of the present disclosure are reactive.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art.

The term "$K_d$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}$H $^{14}$C, $^{35}$S, $^{90}$Y, $^{99}$Tc, $^{111}$In, $^{125}$I, $^{131}$I, $^{177}$Lu, $^{166}$Ho or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent.

The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen-binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, *Crystallization of Nucleic Acids and Proteins, a Practical Approach*, 2nd ed., pp. 20 1-16, Oxford University Press, New York, N.Y., (1999).

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest.

The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence.

The term "control sequences" is intended to include components whose presence is essential for expression and processing, and can also include additional components whose presence is advantageous, for example, leader sequences and fusion partner sequences. "Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein. Preferably, host cells include prokaryotic and eukaryotic cells selected from any of the Kingdoms of life. Preferred eukaryotic cells include protist, fungal, plant and animal cells. Most preferably, host cells include but are not limited to the prokaryotic cell line *E. coli*; mammalian cell lines CHO, HEK 293 and COS; the insect cell line Sf9; and the fungal cell *Saccharomyces cerevisiae*. Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference for any purpose. "Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The terms "regulate" and "modulate" are used interchangeably, and, as used herein, refers to a change or an alteration in the activity of a molecule of interest Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction. Correspondingly, the term "modulator," as used herein, is a compound capable of changing or altering an activity or function of a molecule of interest. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in International Application Publication No. WO 01/83525.

The term "agonist", as used herein, refers to a modulator that, when contacted with a molecule of interest, causes an increase in the magnitude of a certain activity or function of the molecule compared to the magnitude of the activity or function observed in the absence of the agonist.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other mammalian or non-mammalian animals. Such substances include, but are not limited to, blood, serum, urine, synovial fluid, cells, organs, tissues (e.g., brain), bone marrow, lymph nodes, cerebrospinal fluid, and spleen.

Unless otherwise defined herein, scientific and technical terms used in connection with the present disclosure shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms shall include pluralities and plural terms shall include the singular.

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Generally, nomenclatures used in connection with, and techniques of, cell and tissue culture, molecular biology, immunology, microbiology, genetics and protein and nucleic acid chemistry and hybridization described herein are those well known and commonly used in the art.

As used herein, the term "hydrogen peroxide generating enzyme" refers to an enzyme that is capable of producing as a reaction product the chemical compound having the molecular formula $H_2O_2$, i.e. hydrogen peroxide. Non-limiting examples of hydrogen peroxide generating enzymes are listed below in Table A.

TABLE A

| ACCEPTED COMMON NAME | IUBMB ENZYME NOMENCLATURE | PREFERRED SUBSTRATE |
| --- | --- | --- |
| (R)-6-hydroxynicotine oxidase | EC 1.5.3.6 | (R)-6-hydroxynicotine |
| (S)-2-hydroxy acid oxidase | EC 1.1.3.15 | S)-2-hydroxy acid |
| (S)-6-hydroxynicotine oxidase | EC 1.5.3.5 | (S)-6-hydroxynicotine |
| 3-aci-nitropropanoate oxidase | EC 1.7.3.5 | 3-aci-nitropropanoate |
| 3-hydroxyanthranilate oxidase | EC 1.10.3.5 | 3-hydroxyanthranilate |

TABLE A-continued

| ACCEPTED COMMON NAME | IUBMB ENZYME NOMENCLATURE | PREFERRED SUBSTRATE |
|---|---|---|
| 4-hydroxymandelate oxidase | EC 1.1.3.19 | (S)-2-hydroxy-2-(4-hydroxyphenyl)acetate |
| 6-hydroxynicotinate dehydrogenase | EC 1.17.3.3 | 6-hydroxynicotinate |
| Abscisic-aldehyde oxidase | EC 1.2.3.14 | abscisic aldehyde |
| acyl-CoA oxidase | EC 1.3.3.6 | acyl-CoA |
| Alcohol oxidase | EC 1.1.3.13 | a primary alcohol |
| Aldehyde oxidase | EC 1.2.3.1 | an aldehyde |
| amine oxidase | | |
| amine oxidase (copper-containing) | EC 1.4.3.6 | primary monoamines, diamines and histamine |
| amine oxidase (flavin-containing) | EC 1.4.3.4 | a primary amine |
| aryl-alcohol oxidase | EC 1.1.3.7 | an aromatic primary alcohol (2-naphthyl)methanol 3-methoxybenzyl alcohol |
| aryl-aldehyde oxidase | EC 1.2.3.9 | an aromatic aldehyde |
| Catechol oxidase | EC 1.1.3.14 | Catechol |
| cholesterol oxidase | EC 1.1.3.6 | Cholesterol |
| Choline oxidase | EC 1.1.3.17 | Choline |
| columbamine oxidase | EC 1.21.3.2 | Columbamine |
| cyclohexylamine oxidase | EC 1.4.3.12 | Cyclohexylamine |
| cytochrome c oxidase | EC 1.9.3.1 | |
| D-amino-acid oxidase | EC 1.4.3.3 | a D-amino acid |
| D-arabinono-1,4-lactone oxidase | EC 1.1.3.37 | D-arabinono-1,4-lactone |
| D-arabinono-1,4-lactone oxidase | EC 1.1.3.37 | D-arabinono-1,4-lactone |
| D-aspartate oxidase | EC 1.4.3.1 | D-aspartate |
| D-glutamate oxidase | EC 1.4.3.7 | D-glutamate |
| D-glutamate(D-aspartate) oxidase | EC 1.4.3.15 | D-glutamate |
| dihydrobenzophenanthridine oxidase | EC 1.5.3.12 | dihydrosanguinarine |
| dihydroorotate oxidase | EC 1.3.3.1 | (S)-dihydroorotate |
| dihydrouracil oxidase | EC 1.3.3.7 | 5,6-dihydrouracil |
| dimethylglycine oxidase | EC 1.5.3.10 | N,N-dimethylglycine |
| D-mannitol oxidase | EC 1.1.3.40 | Mannitol |
| Ecdysone oxidase | EC 1.1.3.16 | Ecdysone |
| ethanolamine oxidase | EC 1.4.3.8 | Ethanolamine |
| Galactose oxidase | EC 1.1.3.9 | D-galactose |
| Glucose oxidase | EC 1.1.3.4 | β-D-glucose |
| glutathione oxidase | EC 1.8.3.3 | Glutathione |
| Glycerol-3-phosphate oxidase | EC 1.1.3.21 | sn-glycerol 3-phosphate |
| Glycine oxidase | EC 1.4.3.19 | Glycine |
| glyoxylate oxidase | EC 1.2.3.5 | Glyoxylate |
| hexose oxidase | EC 1.1.3.5 | D-glucose, D-galactose D-mannose maltose lactose cellobiose |
| hydroxyphytanate oxidase | EC 1.1.3.27 | L-2-hydroxyphytanate |
| indole-3-acetaldehyde oxidase | EC 1.2.3.7 | (indol-3-yl)acetaldehyde |
| lactic acid oxidase | | Lactic acid |
| L-amino-acid oxidase | EC 1.4.3.2 | an L-amino acid |
| L-aspartate oxidase | EC 1.4.3.16 | L-aspartate |
| L-galactonolactone oxidase | EC 1.3.3.12 | L-galactono-1,4-lactone |
| L-glutamate oxidase | EC 1.4.3.11 | L-glutamate |
| L-gulonolactone oxidase | EC 1.1.3.8 | L-gulono-1,4-lactone |
| L-lysine 6-oxidase | EC 1.4.3.20 | L-lysine |
| L-lysine oxidase | EC 1.4.3.14 | L-lysine |
| long-chain-alcohol oxidase | EC 1.1.3.20 | A long-chain-alcohol |
| L-pipecolate oxidase | EC 1.5.3.7 | L-pipecolate |
| L-sorbose oxidase | EC 1.1.3.11 | L-sorbose |
| malate oxidase | EC 1.1.3.3 | (S)-malate |
| methanethiol oxidase | EC 1.8.3.4 | Methanethiol |
| monoamino acid oxidase | | |
| N$^6$-methyl-lysine oxidase | EC 1.5.3.4 | 6-N-methyl-L-lysine |
| N-acylhexosamine oxidase | EC 1.1.3.29 | N-acetyl-D-glucosamine N-glycolylglucosamine N-acetylgalactosamine N-acetylmannosamine. |
| NAD(P)H oxidase | EC 1.6.3.1 | NAD(P)H |
| nitroalkane oxidase | EC 1.7.3.1 | a nitroalkane |
| N-methyl-L-amino-acid oxidase | EC 1.5.3.2 | an N-methyl-L-amino acid |
| nucleoside oxidase | EC 1.1.3.39 | Adenosine |
| Oxalate oxidase | EC 1.2.3.4 | Oxalate |
| polyamine oxidase | EC 1.5.3.11 | 1-N-acetylspermine |

TABLE A-continued

| ACCEPTED COMMON NAME | IUBMB ENZYME NOMENCLATURE | PREFERRED SUBSTRATE |
|---|---|---|
| polyphenol oxidase | EC 1.14.18.1 | |
| Polyvinyl-alcohol oxidase | EC 1.1.3.30 | polyvinyl alcohol |
| prenylcysteine oxidase | EC 1.8.3.5 | an S-prenyl-L-cysteine |
| Protein-lysine 6-oxidase | EC 1.4.3.13 | peptidyl-L-lysyl-peptide |
| putrescine oxidase | EC 1.4.3.10 | butane-1,4-diamine |
| Pyranose oxidase | EC 1.1.3.10 | D-glucose<br>D-xylose<br>L-sorbose<br>D-glucono-1,5-lactone |
| Pyridoxal 5'-phosphate synthase | EC 1.4.3.5 | pyridoxamine 5'-phosphate |
| pyridoxine 4-oxidase | EC 1.1.3.12 | Pyridoxine |
| pyrroloquinoline-quinone synthase | EC 1.3.3.11 | 6-(2-amino-2-carboxyethyl)-7,8-dioxo-1,2,3,4,5,6,7,8-octahydroquinoline-2,4-dicarboxylate |
| Pyruvate oxidase | EC 1.2.3.3 | Pyruvate |
| Pyruvate oxidase (CoA-acetylating) | EC 1.2.3.6 | Pyruvate |
| Reticuline oxidase | EC 1.21.3.3 | Reticuline |
| retinal oxidase | EC 1.2.3.11 | Retinal |
| Rifamycin-B oxidase | EC 1.10.3.6 | rifamycin-B |
| Sarcosine oxidase | EC 1.5.3.1 | Sarcosine |
| secondary-alcohol oxidase | EC 1.1.3.18 | a secondary alcohol |
| sulfite oxidase | EC 1.8.3.1 | Sulfite |
| superoxide dismutase | EC 1.15.1.1 | Superoxide |
| superoxide reductase | EC 1.15.1.2 | Superoxide |
| tetrahydroberberine oxidase | EC 1.3.3.8 | (S)-tetrahydroberberine |
| Thiamine oxidase | EC 1.1.3.23 | Thiamine |
| tryptophan α,β-oxidase | EC 1.3.3.10 | L-tryptophan |
| urate oxidase (uricase, uric acid oxidase) | EC 1.7.3.3 | uric acid |
| Vanillyl-alcohol oxidase | EC 1.1.3.38 | vanillyl alcohol |
| Xanthine oxidase | EC 1.17.3.2 | Xanthine |
| xylitol oxidase | EC 1.1.3.41 | Xylitol |

The methods and techniques of the present disclosure are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

According to the invention and, in particular, for the purpose of assessing the binding affinities of the antibodies of the present disclosure, a process may be used as described in International Application Publication No. WO 2004/067561, which is incorporated herein by reference in its entirety. The process comprises unfolding a natural, recombinant or synthetic peptide or a derivative thereof; exposing the at least partially unfolded peptide or derivative thereof to a detergent, reducing the detergent action and continuing incubation. For the purpose of unfolding the peptide, hydrogen bond breaking agents such as, for example, hexafluoroisopropanol (HFIP) may be allowed to act on the protein. Times of action of a few minutes, for example about 10 to 60 minutes, are sufficient when the temperature of action is from about 20 to 50° C. and in particular about 35 to 40° C. Subsequent dissolution of the residue evaporated to dryness, preferably in concentrated form, in suitable organic solvents miscible with aqueous buffers, such as, for example, dimethyl sulfoxide (DMSO), results in a suspension of the at least partially unfolded peptide or derivative thereof, which can be used subsequently. If required, the stock suspension may be stored at low temperature, for example at about −20° C., for an interim period. Alternatively, the peptide or the derivative thereof may be taken up in slightly acidic, preferably aqueous, solution, for example, an about 10 mM aqueous HCl solution. After an incubation time of usually a few minutes, insoluble components are removed by centrifugation. A few minutes at 10000 g is expedient. These method steps are preferably carried out at room temperature, i.e. a temperature in the range from 20° C. to 30° C. The supernatant obtained after centrifugation contains the peptide or the derivative thereof and may be stored at low temperature, for example at about −20° C., for an interim period.

B. Preparation of Monoclonal Antibodies

Monoclonal antibodies can be prepared using a wide variety of techniques known in the art including the use of hybridoma, recombinant, and phage display technologies, or a combination thereof. For example, it is preferred that monoclonal antibodies of the present disclosure be produced using hybridoma techniques including those known in the art and taught, for example, in Harlow et al., *Antibodies: A Laboratory Manual* (Cold Spring Harbor Laboratory Press, 2nd ed. 1988); Hammerling, et al., in: *Monoclonal Antibodies and T-Cell Hybridomas* 563-681 (Elsevier, N.Y., 1981) (said references incorporated by reference in their entireties).

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present disclosure provides methods of generating monoclonal antibodies as well as antibodies produced by the method comprising culturing a hybridoma cell secreting an antibody of the present disclosure wherein, preferably, the hybridoma is generated by fusing splenocytes isolated from a mouse immunized with an antigen of the present disclosure with myeloma cells and then screening the hybridomas resulting from the fusion for hybridoma clones that secrete an antibody able to bind a polypeptide of the present disclosure. Briefly, mice can be immunized with the antigen of interest. In a preferred embodiment, the antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with the antigen, antibodies and/or antibody-producing cells may be obtained from the animal. An antibody-containing serum is obtained from the animal by bleeding or sacrificing the animal. The serum may be used as it is obtained from the animal, an immunoglobulin fraction may be obtained from the serum, or the antibodies may be purified from the serum. Serum or immunoglobulins obtained in this manner are polyclonal, thus having a heterogeneous array of properties.

Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (Manassas, Va.). Hybridomas are selected and cloned by limited dilution. The hybridoma clones are then assayed by methods known in the art for cells that secrete antibodies capable of binding to the peptide or antigen of interest. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using the antigen, or a portion thereof, or a cell expressing the antigen. In a preferred embodiment, the initial screening is performed using an enzyme-linked immunoassay (ELISA) or a radioimmunoassay (RIA), preferably an ELISA. An example of ELISA screening is provided in International Application Publication No. WO 00/37504, herein incorporated by reference.

Antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing the antibody.

C. Other Methods of Producing Antibodies

As noted above, antibodies of the present disclosure may be produced by any of a number of techniques known in the art. For example, the antibody may be produced based upon expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although, it is possible to express the antibodies of the present disclosure in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the present disclosure include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present disclosure. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the present disclosure. In addition, bifunctional antibodies may be produced in which one heavy and one light chain are an antibody of the present disclosure and the other heavy and light chain are specific for an antigen other than the antigens of interest by crosslinking an antibody of the present disclosure to a second antibody by standard chemical crosslinking methods.

In a preferred system for recombinant expression of an antibody, or antigen-binding portion thereof, of the present disclosure, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the present disclosure by culturing a host cell of the present disclosure in a suitable culture medium until a recombinant antibody of the present disclosure is synthesized. The method can further comprise isolating the recombinant antibody from the culture medium.

D. Preparation of Antibodies for Diagnostic and Other Applications

As noted above, preferably, antibodies of the present disclosure exhibit a high binding affinity to one or more epitopes of PIVKA-II, e.g., as assessed by any one of several in vitro and in vivo assays known in the art (e.g., see examples below).

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260 and 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases, these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcyRs and complement C1q, respectively. Neonatal Fc receptors (FcRn) are the critical components determining the circulating half-life of antibodies. In still another embodiment, at least one amino acid residue is replaced in the constant region of the antibody, for example the Fc region of the antibody, such that effector functions of the antibody are altered.

One embodiment provides a labeled binding protein wherein an antibody or antibody portion of the present disclosure is derivatized or linked to another functional molecule (e.g., another peptide or protein). For example, a labeled binding protein of the present disclosure can be derived by functionally linking an antibody or antibody portion of the present disclosure (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Immunoassays according to the present disclosure employ one or more anti-PIVKA-II antibodies, each of which binds specifically to PIVKA-II. In certain embodiments, an antibody as disclosed herein has a detectable label. Detectable labels suitable for use in the detection antibodies of the present disclosure include any compound or composition having a moiety that is detectable by spectroscopic, photochemical, biochemical, immunochemical, electrical, optical, or chemical means. Such labels include, for example, an enzyme, oligonucleotide, nanoparticle chemiluminophore, fluorophore, fluorescence quencher, chemiluminescence quencher, or biotin. Thus for example, in an immunoassay employing an optical signal, the optical signal is measured as an analyte concentration dependent change in chemiluminescence, fluorescence, phosphorescence, electrochemiluminescence, ultraviolet absorption, visible absorption, infrared absorption, refraction, surface plasmon resonance. In an immunoassay employing an electrical signal, the electrical signal is measured as an analyte concentration dependent change in current, resistance, potential, mass to charge ratio, or ion count. In an immunoassay employing a change-of-state signal, the change of state signal is measured as an analyte concentration dependent change in size, solubility, mass, or resonance.

Useful labels according to the present disclosure include magnetic beads (e.g., Dynabeads™), fluorescent dyes (e.g., fluorescein, Texas Red, rhodamine, green fluorescent protein) and the like (see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., 3H, 125I, 35S, 14C, or 32P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to each antibody prior to, or during, or after contact with the biological sample. So-called "direct labels" are detectable labels that are directly attached to or incorporated into the detection antibody prior to use in the assay. Direct labels can be attached to or incorporated into the antibody by any of a number of means well known to those of skill in the art. In contrast, so-called "indirect labels" typically bind to each antibody at some point during the assay. Often, the indirect label binds to a moiety that is attached to or incorporated into the detection agent prior to use. Thus, for example, each antibody can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542). Such polypeptides can thus be labeled and added to the assay mixture, where they will bind to each antibody, as well as to the autoantibodies, labeling all and providing a composite signal attributable to analyte and autoantibody present in the sample.

Some labels useful in the present disclosure may require the use of an additional reagent(s) to produce a detectable signal. In an ELISA, for example, an enzyme label (e.g., beta-galactosidase) will require the addition of a substrate (e.g., X-gal) to produce a detectable signal. In immunoassays using an acridinium compound as the direct label, a basic solution and a source of hydrogen peroxide are added.

In an exemplary embodiment, a chemiluminescent compound is used as a direct label conjugated to an antibody. The chemiluminescent compound can be for example an acridinium compound. When an acridinium compound is used as the detectable label, then the above-described method may further include generating or providing a source of hydrogen peroxide to the mixture resulting from contacting the test sample with the labeled antibody, and adding at least one basic solution to the mixture to generate a light signal. The light signal generated or emitted by the mixture is then measured to detect the PIVKA-II in the test sample.

The source of hydrogen peroxide may be a buffer solution or a solution containing hydrogen peroxide or an enzyme that generates hydrogen peroxide when added to the test sample. The basic solution serves as a trigger solution, and the order in which the at least one basic solution and detectable label are added is not critical. The basic solution used in the method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the test sample depends on the concentration of the basic solution used in the assay. Based on the concentration of the basic solution used, one skilled in the art could easily determine the amount of basic solution to be used in the method described herein.

In a chemiluminescence immunoassay according to the present disclosure and using an acridinium compound as the detectable label, preferably the acridinium compound is an acridinium-9-carboxamide. Specifically, the acridinium-9-carboxamide has a structure according to formula I:

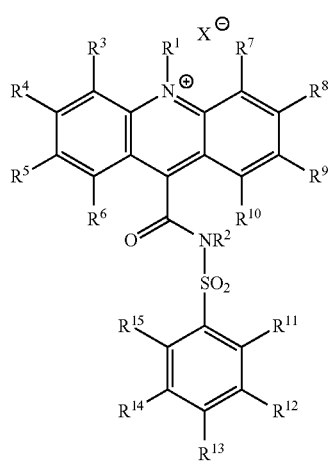

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^\ominus$ is an anion.

Methods for preparing acridinium 9-carboxamides are described in Mattingly, P. G. *J. Biolumin. Chemilumin.*, 6, 107-14; (1991); Adamczyk, M.; Chen, Y.-Y., Mattingly, P. G.; Pan, Y. *J. Org. Chem.*, 63, 5636-5639 (1998); Adamczyk, M.; Chen, Y.-Y.; Mattingly, P. G.; Moore, J. A.; Shreder, K. *Tetrahedron*, 55, 10899-10914 (1999); Adamczyk, M.; Mattingly, P. G.; Moore, J. A.; Pan, Y. *Org. Lett.*, 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.*, 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.*, 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

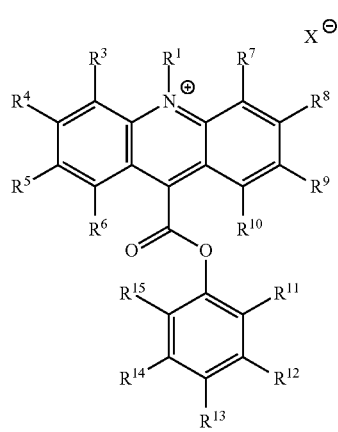

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence*, 15:245-249 (2000); Razavi, Z et al., *Luminescence*, 15:239-244 (2000); and U.S. Pat. No. 5,241, 070 (each incorporated herein by reference in their entireties for their teachings regarding same).

Another embodiment of the present disclosure provides a crystallized binding protein. Preferably, the invention relates to crystals of whole antibodies and fragments thereof as disclosed herein, and formulations and compositions comprising such crystals. In one embodiment the crystallized binding protein has a greater half-life in vivo than the soluble counterpart of the binding protein. In another embodiment, the binding protein retains biological activity after crystallization. Crystallized binding protein of the present disclosure may be produced according methods known in the art and as disclosed in International App. Publication No. WO 02/072636, incorporated herein by reference. Another embodiment of the present disclosure provides a glycosylated binding protein wherein the antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO Jr.* (1991) 10:2717 2723).

One aspect of the present disclosure is directed to generating glycosylation site mutants in which the 0- or N-linked glycosylation site of the binding protein has been mutated. One skilled in the art can generate such mutants using standard well-known technologies. The creation of glycosylation site mutants that retain the biological activity but have increased or decreased binding activity are another object of the present disclosure.

In still another embodiment, the glycosylation of the antibody or antigen-binding portion of the present disclosure is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in International App. Publication No. WO 03/016466A2, and U.S. Pat. Nos. 5,714,350 and 6,350,861, each of which is incorporated herein by reference in its entirety.

Additionally or alternatively, a modified antibody of the present disclosure can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present disclosure to thereby produce an antibody with altered glycosylation. See, for example, Shields, R. L. et al. (2002) *J. Biol. Chem.* 277: 26733-26740; Umana et al. (1999) *Nat. Biotech.* 17:176-1, as well as, European Patent NO.: EP 1,176,195; International App. Publication Nos. WO 03/035835 and WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S Patent Application Publication Nos. 20040018590 and 20020137134 and International App. Publication No. WO 05/100584 A2).

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507,050 and incorporated herein by reference.

One aspect of the present disclosure pertains to a DVD binding protein comprising binding proteins capable of binding to one or more epitopes of PIVKA-II. Preferably, the DVD binding protein is capable of binding the epitope and a second target.

In addition to the binding proteins, the present invention is also directed to an anti-idiotypic (anti-Id) antibody specific for such binding proteins of the present disclosure. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

E. Methods Using the Antibodies

Given their ability to bind to PIVKA-II, or epitopes or portions thereof, the antibodies of as disclosed herein can be used to detect and/or quantify an amount of PIVKA-II in a biological sample (such as, for example, serum, blood, tissue or plasma), using a conventional competitive or non-competitive immunoassay (e.g., an enzyme linked immunosorbent assay (ELISA), a radioimmunoassay (RIA), immunometric, sandwich assay or tissue immunohistochemistry). Such detection may then result in a diagnosis of HCC or liver cancer for the patient from which the biological sample was obtained.

A method for detecting PIVKA-II in a biological sample comprises, for example, contacting a biological sample with an antibody of the present disclosure (or an antibody portion thereof), and detecting PIVKA-II or a portion (e.g., epitope thereof) by detecting formation of an antigen/antibody complex, for a time and under conditions sufficient for the formation of first antibody-antigen complexes. The antibody may be directly or indirectly labeled with a detectable substance to facilitate detection and/or quantification of the bound or unbound antigen (i.e., PIVKA-II).

A method of detecting PIVKA-II antigen in a test sample may alternatively comprise the steps of: a) contacting the test sample with a first antibody having an antigen binding portion that binds to amino acids 13-27 of PIVKA-II, for a time and under conditions sufficient for the formation of first antibody-antigen complexes; b) adding a second antibody to the first antibody/antigen complexes, wherein the second antibody has an antigen binding portion that binds to amino acids 1-13 of PIVKA-II and is conjugated to a detectable label, for a time and under conditions sufficient to form first antibody/antigen/second antibody complexes; and c) measuring the signal generated by or emitted from the detectable label and detecting the PIVKA-II antigen in the test sample. The first antibody is for example mAb 3C10, i.e., a monoclonal antibody produced by a hybridoma cell line having ATCC deposit designation PTA-9638. The second antibody is for example 6H6, i.e., a monoclonal antibody produced by a hybridoma cell line having ATCC deposit designation PTA-10541.

Quantification methods based on immunoassays are well-known and may include for example comparing the amount of PIVKA-II as determined from the immunoassay output to a predetermined level such as a threshold or cut-off value, above which a level of PIVKA-II is indicative of HCC or liver cancer. An exemplary threshold or cut-off level is about 40 mAU/mL but can range up to about 100 mAU/mL (0.1 AU/mL) for a human subject. For example, the cut-off level can be about 50, about 60, about 70, about 80, or about 90 mAU/mL. It will be appreciated that the predetermined cut-off value used may vary based on many factors including the age, gender, ethnicity, and clinical history of the subject.

A method of diagnosing HCC or liver cancer in a patient suspected of having HCC or liver cancer can thus comprise, for example, the steps of: a) isolating a biological sample from the patient; b) contacting the biological sample with an antibody comprising an antigen binding portion that binds to amino acids 1-13 of PIVKA-II antigen for a time and under conditions sufficient for formation of PIVKA-II antigen/antibody complexes; c) detecting presence of the PIVKA-II antigen/antibody complexes; d) dissociating the PIVKA-II antigen present in the complexes from the antibody present in the complexes; and e) measuring the amount of dissociated PIVKA-II antigen, wherein an amount of PIVKA-II antigen greater than a predetermined level indicates a diagnosis of HCC or liver cancer in the patient. The predetermined level can be for example about 40 mAU/mL, but can a higher level up to about as 100 mAU/mL as explained above. Alternatively, a method of diagnosing HCC or liver cancer in a patient can comprise the steps of: a) isolating a biological sample from the patient; b) contacting the biological sample with an antibody comprising an antigen binding portion that binds to amino acids 1-13 of PIVKA-II antigen for a time and under conditions sufficient for formation of PIVKA-II antigen/antibody complexes; and c) detecting presence of the PIVKA-II antigen/antibody complexes; d) dissociating the PIVKA-II antigen present in the complexes from the antibody present in the complexes; and e) measuring the amount of dissociated PIVKA-II antigen, wherein an amount of dissociated PIVKA-II antigen greater than a predetermined level indicates a diagnosis of HCC or liver cancer in the patient.

Alternatively, a method of diagnosing HCC or liver cancer in a patient can comprise the use of two or more anti-PIVKA antibodies. For example, such a method can comprise the steps of: a) isolating a biological sample from the patient; b) contacting the biological sample with a first antibody having an antigen binding domain that binds to amino acids 13-27 of PIVKA-II antigen for a time and under conditions sufficient for the formation of PIVKA-II antigen/antibody complexes; c) adding a conjugate to the resulting PIVKA-II antigen/antibody complexes for a time and under conditions sufficient to allow the conjugate to bind to the bound PIVKA-II antigen, wherein the conjugate comprises a second antibody having an antigen binding domain that binds to amino acids 1-13 of PIVKA-II and is attached to a detectable label capable of generating a detectable signal; d) detecting the presence of PIVKA-II antigen which may be present in the biological sample by detecting a signal generated by the detectable label; and e) measuring the amount of PIVKA-II antigen present in the test sample by measuring the intensity of the signal, wherein an amount of PIVKA-II antigen greater than a predetermined level is indicative of the presence of HCC or liver cancer in the patient. In the method, the predetermined level can be about 40 mAU/mL, but can a higher level up to about as 100 mAU/mL as explained above. The first antibody can be a monoclonal antibody produced by the hybridoma cell line having ATCC deposit designation PTA-9638 (mAb 3C10), and the second antibody can be a monoclonal antibody produced by the hybridoma cell line having ATCC deposit designation PTA-10541. The first antibody can be immobilized on a solid phase either before or after the formation of the first antibody-antigen complexes.

The methods encompass thus use of at least two different binding proteins that bind to PIVKA-II, wherein each binding protein comprises an antigen binding portion that specifically binds to a subset of amino acids 1-33 of PIVKA-II, and wherein the antigen binding portion of each binding protein binds to a different subset of amino acids 1-33 of PIVKA-II. For example, a method using two binding proteins can use a first monoclonal antibodies such as mAb 3C10 which has an antigen binding portion that binds to PIVKA-II (i.e., an antibody produced by the hybridoma cell line designated by American Type Culture Collection (ATCC) deposit designation PTA-9638), and a second monoclonal antibody such as 6H6 that has an antigen binding portion that binds to PIVKA-II and also an antigen binding portion that binds to at least a subset of amino acids 1-33 of prothrombin (i.e., an antibody produced by the hybridoma cell line designated by American Type Culture Collection (ATCC) deposit PTA-10541). The use of at least two different antibodies that are both capable of specific binding to PIVKA-II but have different antigen binding domains and bind to different subsets of the amino acids 1-33 of the PIVKA-II protein will produce a much higher signal than use of a single monoclonal antibody.

Suitable detectable substances for labeling the antibody include various enzymes, prosthetic groups, fluorescent materials, luminescent materials and radioactive materials. Examples of suitable enzymes include horseradish peroxidase, alkaline phosphatase, p-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a radionuclides (e.g. $^{3}$H, $^{14}$C, $^{35}$S, $^{90}$Y, $^{99}$Tc, $^{111}$In, $^{125}$I, $^{131}$I, $^{177}$Lu, $^{166}$Ho or $^{153}$Sm).

As an alternative to labeling the antibody, the antigen can be assayed in biological fluids by a competition immunoassay utilizing recombinant standards labeled with a detectable substance and an unlabeled antibody. In this assay, the biological sample, the labeled recombinant antigen standard and the antibody are combined, and the amount of labeled peptide standard bound to the unlabeled antibody is determined. The amount of antigen in the biological sample is inversely proportional to the amount of labeled antigen standard bound to the antibody. In this method, the antibody can comprise an antigen-binding domain that binds to amino acids 1-13 of PIVKA-II, i.e., 6H6, a monoclonal antibody produced by a hybridoma cell line having ATCC deposit designation PTA-10541.

To illustrate the above assays in connection with the present disclosure, an antibody to PIVKA-II (or to epitopes or portions of full length PIVKA-II), such as 6H6 (or mAb 3C10), is for example coated on a solid phase (or is present in a liquid phase). The test or biological sample (e.g., serum, plasma, urine, etc.) is then contacted with the solid phase. If PIVKA-II antigen is present in the sample, the antibody bound to the solid phase will bind to the PIVKA-II antigen which may then be detected by either a direct or indirect method. The direct method comprises simply detecting presence of the complex itself and thus presence of the PIVKA-II antigen. In the indirect method, a conjugate is added to the bound PIVKA-II antigen. The conjugate comprises a second antibody (usually different from the first antibody coated onto the solid phase), which binds to the bound PIVKA-II antigen, attached to a signal generating compound or label. Should the second antibody bind to the bound antigen, the signal-generating compound generates a measurable signal. Such signal then indicates presence of the antigen in the test sample. It should be noted that the initial capture antibody (for detecting PIVKA-II antigens) used in the immunoassay may be covalently or non-covalently (e.g., ionic, hydrophobic, etc.) attached to the solid phase Linking agents for covalent attachment are known in the art and may be part of the solid phase or derivatized to it prior to coating.

Examples of solid phases used in diagnostic immunoassays are porous and non-porous materials, latex particles, magnetic particles, microparticles (see U.S. Pat. No. 5,705, 330), beads, membranes, microtiter wells and plastic tubes. The choice of solid phase material and method of labeling the antigen or antibody present in the conjugate, if desired, are determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is itself detectable or may be reacted with one or more additional compounds to generate a detectable product. Examples of signal-generating compounds include chromogens, radioisotopes (e.g., 125I, 131I, 32P, 3H, 35S and 14C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Examples of biological fluids which may be tested by the above immunoassays include plasma, urine, whole blood, dried whole blood, serum, cerebrospinal fluid, saliva, tears, nasal washes or aqueous extracts of tissues and cells.

Alternatively, in order to detect the presence of PIVKA-II in a biological sample, one may coat the solid phase with PIVKA-II antigen and then contact the solid phase with labeled antibody to PIVKA-II antigen, such as monoclonal antibody 6H6 (or mAb 3C10), for a time and under conditions sufficient to allow the immobilized antigen to bind to the labeled antibody. Subsequent thereto, the test sample may be added to the antigen-antibody complex. If PIVKA-II is present in the test sample, it will then bind to the bound labeled antibody. A detectable signal is then generated by the label indicating presence of the PIVKA-II antigen in the test sample.

Additionally, in an alternative assay format, one may use a PIVKA-II recombinant standard labeled with a detectable substance and an unlabeled antibody such as 6H6 (or mAb 3C10). In this assay, the biological test sample, the labeled recombinant PIVKA-II antigen standard and the 6H6 (or mAb 3C10) monoclonal antibody are combined, and the amount of labeled PIVKA-II standard bound to the unlabeled antibody is determined. The amount of PIVKA-II antigen in the biological sample is inversely proportional to the amount of labeled PIVKA-II antigen standard bound to the antibody.

Other assay formats which may be used for purposes of the present disclosure, in order to simultaneously detect antigens and antibodies include, for example, Dual assay strip blots, a rapid test, a Western blot, as well as the use of paramagnetic particles in, for example, an Architect® assay (Frank Quinn, The Immunoassay Handbook, Second edition, edited by David Wild, pages 363-367, 2001). Such formats are known to those of ordinary skill in the art.

It should also be noted that the elements of the assays described above are particularly suitable for use in the form of a kit. The kit may also comprise one container such as vial, bottles or strip, with each container with a pre-set solid phase, and other containers containing the respective conjugates. These kits may also contain vials or containers of other reagents needed for performing the assay, such as washing, processing and indicator reagents.

Any of the exemplary formats herein and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

Additionally, the assays and kits of the present invention optionally can be adapted or optimized for point of care assay systems, including Abbott's Point of Care (i-STATIm) electrochemical immunoassay system. Immunosensors and methods of manufacturing and operating them in single-use test devices are described, for example in U.S. Pat. No. 5,063, 081 and published U.S. Patent Application Nos. 20030170881, 20040018577, 20050054078, and 20060160164 (incorporated by reference herein for their teachings regarding same).

Further, it has been noted that PIVKA-II may induce malignancy of a tumor (Shiraha, *J. Biol. Chem.* 2005 Feb. 25; 280(8):6409-15). Thus, the present disclosure also provides methods for reducing PIVKA-II activity, in a human suffering from a disease or disorder with which PIVKA-II activity is associated (e.g., liver cancer or HCC). This method comprises administering to the subject an antibody (i.e., 6H6) or portion thereof (e.g., Fab' fragment) of the present disclosure such that PIVKA-II activity in the subject is reduced (i.e., passive immunization). Moreover, an antibody of the present disclosure (or fragment thereof) can be administered to a non-human mammal for therapeutic purposes, other veterinary purposes or for study of the effect of the antibody in an animal having a condition mimicking that found in humans. In particular, such animal models may be useful for evaluating the therapeutic efficacy of antibodies of the present disclosure (e.g., testing of dosages and time courses of administration).

Non-limiting examples of disorders that can be treated with the antibodies of the present disclosure include those disorders discussed in the section below pertaining to pharmaceutical compositions of the antibodies of the present disclosure.

F. Pharmaceutical Compositions

As noted above, the invention also provides pharmaceutical compositions comprising an antibody, or antigen-binding portion thereof, of the present disclosure and a pharmaceutically acceptable carrier. A pharmaceutical composition may comprise for example a binding protein having an antigen binding portion that binds to amino acids 1-13 of PIVKA-II. The binding protein may be a monoclonal antibody as described herein, for example a monoclonal antibody produced by a hybridoma cell line designated by American Type Culture Collection (ATCC) deposit designation PTA-10541. The pharmaceutical compositions comprising antibodies of the present disclosure are for use in, but not limited to, diagnosing, detecting, or monitoring a disorder, in preventing, treating, managing, or ameliorating of a disorder or one or more symptoms thereof, and/or in research. The pharmaceutical compositions can be used for example for use in treating or diagnosing cancer such as HCC or liver cancer. A pharmaceutical composition may comprise one or more antibodies of the present disclosure. In another embodiment, the pharmaceutical composition comprises one or more antibodies of the present disclosure and one or more prophylactic or therapeutic agents other than antibodies of the present disclosure for treating a disorder in which PIVKA-II activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the present disclosure can be incorporated into pharmaceutical compositions suitable for administration to a subject. Typically, the pharmaceutical composition comprises an antibody (e.g., 6H6) or antibody portion of the present disclosure and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the present disclosure or the combination of one or more antibodies of the present disclosure and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor mediated endocytosis (see, e.g., Wu and Wu, *J. Biol. Chem.* 262:4429-4432 (1987)), construction of a nucleic acid as part of a retroviral or other vector, etc. Methods of administering a prophylactic or therapeutic agent of the present disclosure include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934, 272, 5,874,064, 5,855,913, 5,290,540, and 4,880,078; and International App. Publication Nos. WO 92/19244, WO 97/32572, WO 97/44013, WO 98/31346, and WO 99/66903, each of which is incorporated herein by reference their entireties. In one embodiment, an antibody as disclosed herein, combination therapy, or a composition as presently disclosed is administered using Alkermes AIR® pulmonary drug delivery technology (Alkermes, Inc., Cambridge, Mass.). In a specific embodiment, prophylactic or therapeutic agents of the present disclosure are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the present disclosure locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the present disclosure is administered locally to the affected area to a subject to prevent, treat, manage, and/or ameliorate a disorder or a symptom thereof. In another embodiment, an effective amount of one or more antibodies of the present disclosure is administered locally to the affected area of a subject, in combination with an effective amount of one or more therapies (e.g., one or more prophylactic or therapeutic agents) other than an antibody of the present disclosure, to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, 1987, *CRC Crit. Ref Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the therapies of the present disclosure (see e.g., *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; International App. Publication No. WO 99/15154; and International App. Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in *Medical Applications of Controlled Release*, supra, vol. 2, pp. 115-138 (1984)).

Controlled release systems are discussed in the review by Langer (1990, *Science* 249:1527-1533). Any technique known to one of skill in the art can be used to produce sustained release formulations comprising one or more therapeutic agents of the present disclosure. See, e.g., U.S. Pat. No. 4,526,938, International App. Publication No. WO 91/05548, International App. Publication No. WO 96/20698, Ning et al., 1996, "Intratumoral Radioimmunotherapy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397, Cleek et al., 1997, "Biodegradable Polymeric Carriers for a bFGF Antibody for Cardiovascular Application," *Pro. Intl. Symp. Control. Rel. Bioact. Matter.* 24:853-854, and Lam et al., 1997, "Microencapsulation of Recombinant Humanized Monoclonal Antibody for Local Delivery," *Proc. Int'l. Symp. Control Rel. Bioact. Matter.* 24:759-760, each of which is incorporated herein by reference in their entireties.

In a specific embodiment, where the composition of the present disclosure is a nucleic acid encoding a prophylactic or therapeutic agent, the nucleic acid (encoded an antibody of the present disclosure) can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the present disclosure is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lidocaine to ease pain at the site of the injection.

If the compositions of the present disclosure are to be administered topically, the compositions can be formulated in the form of an ointment, cream, transdermal patch, lotion, gel, shampoo, spray, aerosol, solution, emulsion, or other form well known to one of skill in the art. See, e.g., Remington's Pharmaceutical Sciences and Introduction to *Pharmaceutical Dosage Forms,* 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the method according to the present disclosure comprises intranasal administration of a composition, the composition can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the present disclosure comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the present disclosure may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and International App. Publication Nos. WO 92/19244, WO 97/32572, WO 97/44013, WO 98/31346, and WO 99/66903, each of which is incorporated herein by reference their entireties. In a specific embodiment, an antibody of the present disclosure, combination therapy, and/or composition of the present disclosure is administered using Alkermes AIR® pulmonary drug delivery technology (Alkermes, Inc., Cambridge, Mass.).

The method of the present disclosure may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the present disclosure may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the present disclosure encompass administration of W compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the present disclosure is packaged in a hermetically sealed container such as an ampoule or sachette indicating the quantity of the agent. In one embodiment, one or more of the prophylactic or therapeutic agents, or pharmaceutical compositions of the present disclosure is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the present disclosure is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the present disclosure should be stored at between 2° C. and 8° C. in its original container and the prophylactic or therapeutic agents, or pharmaceutical compositions of the present disclosure should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the present disclosure is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody portions of the present disclosure can be incorporated into a pharmaceutical composition suitable for parenteral administration. Preferably, the antibody or antibody portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the present disclosure prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (See International App. Publication No. WO 04/078140 and U.S. Patent App. Publication No. US2006104968, incorporated herein by reference.)

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection.

In another preferred embodiment, the antibody is W administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid.

Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. In certain embodiments, an antibody or antibody portion of the present disclosure may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the present disclosure by other than parenteral administration, it may be necessary to coat the compound with, or co-administer the compound with, a material to prevent its inactivation.

Supplementary active compounds can also be incorporated into the compositions. In certain embodiments, an antibody or antibody portion of the present disclosure is coformulated with and/or coadministered with one or more additional therapeutic agents that are useful for treating disorders in which PIVKA-II activity is detrimental. For example, an anti-PIVKA-II antibody or antibody portion of the present disclosure may be coformulated and/or coadministered with one or more additional antibodies that bind other targets (e.g., antibodies that bind other cytokines or that bind cell surface molecules).

Furthermore, one or more antibodies of the present disclosure may be used in combination with two or more of the foregoing therapeutic agents. Such combination therapies may advantageously utilize lower dosages of the administered therapeutic agents, thus avoiding possible toxicities or complications associated with the various monotherapies. In certain embodiments, an antibody to PIVKA-II or fragment thereof is linked to a half-life extending vehicle known in the art. Such vehicles include, but are not limited to, the Fc domain, polyethylene glycol, and dextran. Such vehicles are described, e.g., in U.S. patent application Ser. No. 09/428,082 and published International Patent Application No. WO 99/25044, which are hereby incorporated by reference for any purpose.

In a specific embodiment, nucleic acid sequences comprising nucleotide sequences encoding an antibody of the present disclosure or another prophylactic or therapeutic agent of the present disclosure are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the present disclosure, the nucleic acids produce their encoded antibody or prophylactic or therapeutic agent of the present disclosure that mediates a prophylactic or therapeutic effect. Any of the methods for gene therapy available in the art can be used according to the present disclosure. For general reviews of the methods of gene therapy, see Goldspiel et al., 1993, *Clinical Pharmacy* 12:488-505; Wu and Wu, 1991, Biotherapy 3:87-95; Tolstoshev, 1993, Ann. *Rev. Pharmacol. Toxicol.* 32:573-596; Mulligan, *Science* 260:926-932 (1993); and Morgan and Anderson, 1993, Ann. Rev. Biochem. 62:191-217; May, 1993, *TIBTECH* 11(5):155-215. Methods commonly known in the art of recombinant DNA technology which can be used are described in Ausubel et al. (eds.), *Current Protocols in Molecular Biology*, John Wiley & Sons, NY (1993); and Kriegler, *Gene Transfer and Expression, A Laboratory Manual*, Stockton Press, NY (1990). An detailed description of various methods of gene therapy is provided for example in U.S. Patent Application Publication No. US20050042664 A1, which is incorporated herein by reference in its entirety.

Antibodies of the present disclosure or antigen binding portions thereof can be used alone or in combination to treat diseases associated with the liver. For example, the antibody may be used as a targeted therapy to prevent autocline cancer growth, and may be attached to a toxic, chemotherapeutic agent (i.e., small molecule or large molecule having cytotoxic properties). Further, the antibody may be labeled for imaging purposes. It should be understood that the antibodies of the present disclosure or antigen binding portion thereof can be used alone or in combination with one or more additional agents, e.g., a therapeutic agent (for example, a small molecule or biologic), said additional agent being selected by the skilled artisan for its intended purpose. The additional agent also can be an agent that imparts a beneficial attribute to the therapeutic composition e.g., an agent that affects the viscosity of the composition. It should further be understood that the combinations which are to be included within this invention are those combinations useful for their intended purpose. The agents set forth below are illustrative for purposes and not intended to be limited. The combinations, which are part of this invention, can be the antibodies of the present disclosure and at least one additional agent selected from the lists below. The combination can also include more than one additional agent, e.g., two or three additional agents if the combination is such that the formed composition can perform its intended function.

The pharmaceutical compositions of the present disclosure may include a "therapeutically effective amount" or a "prophylactically effective amount" of an antibody or antibody portion of the present disclosure. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the present disclosure is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

G. Adaptations of the Compositions and Methods of the Present Disclosure

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that the use of such terms and expressions exclude any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLES

By way of example, and not of limitation, examples of the present disclosures shall now be given.

Example 1

Development of the 6H6 Monoclonal Antibody

Design of immunogen: A seventeen mer peptide in the PIVKA-II (i.e., Protein induced by Vitamin K in absence of blood coagulation Factor II) specific region of PIVKA-II 1-17 was selected as immunogen. There were 4 decarboxylated amino acids of Glutamic acid in the 17 mer peptide in PIVKA-II, while prothrombin (factor-II) had 4 carboxylated glutamic acid (GLA) in the 17 mer peptide. The PIVKA-II specific 17 mer peptide, with the C-terminus cysteine was selectively conjugated to maleimide activated keyhole limpet hemocyanin (KLH). The use of PIVKA-II (1-17) C-terminal conjugated-KLH presents the N-terminal portion of the PIVKA-II as the antigen. Synthesis of the peptide and conjugation to the KLH was conducted with a standard method. The N-terminal region of the peptide was bound to the KLH. The 6H6 monoclonal antibody was produced using the following synthetic peptide (SEQ ID NO: 18) linked to keyhole limpet hemocyanin (KLH) as a carrier.

Peptide sequence for immunization

N-terminal   1 2 3 4 5 6 7 8 9 10 11 12 13 14 15 16 17
PIVKA-II peptide   A N T F L E E V R K G N L E R E C
                                                    |
                                                  KLH Immunization: Peptide KLH was used to immunize three germinal center-associated DNA primase (GANP) transgenic Balb/c mice and three GANP transgenic C57BL/6 mice as shown in FIG. 1. The method of GANP transgenic mice production and method of immunization were followed in accordance with the method described in Sakaguchi et al., *The Journal of Immunology* 174 (2005), pages 4485-4494. Reactivity determination to PIVKA-II and Prothrombin: PIVKA-II antigen was prepared by heating dried prothrombin powder (Sigma F5132) at 110° C. for 8 hours. (See Bajaj et al., J. Biol. Chem. (1982 Apr. 10), 257(7), pages 3726-31.) After more than 8 weeks from immunization, mouse serum was bled and reactivity to PIVKA-II and reactivity to prothrombin were determined using the following procedures:

One ug/mL of PIVKA-II or 5 ug/mL of Prothrombin were added into the 96 wells of an Enzyme Immunoassay (EIA) plate, and PIVKA-II or prothrombin was coated onto the well surface. After blocking by a solution including Block Ace, mouse serum was diluted and then added to the wells. After a washing step, anti-mouse antibody labeled by horseradish peroxidase (HRP) was added. After another washing step, substrate solution was added, and then absorbance was measured by spectrophotometer. Mice that showed the highest reactivity to PIVKA-II and the lowest reactivity to Prothrombin in each group were selected for the next step.

Fusion: Spleen cells from the 1 mouse selected from each group GANP transgenic Balb/c, and GANP transgenic C57BL/6 were fused to myeloma cells with a standard method as described in Sakaguchi et al., *The Journal of Immunology* 174 (2005), pages 4485-4494. The hybridoma cells were diluted by a limiting dilution method, and then the culture supernatant was used for the screening of the hybridomas.

Screening of Hybridoma: Screening of the hybridomas was performed by use of the following procedures: (1) Reactivity to PIVKA-II: One ug/mL of PIVKA-II was added into the 96 well EIA plate, and PIVKA-II was coated onto the well surface. After blocking by a solution including Block Ace, supernatants of the hybridomas were then added to the wells. After a washing step, anti-mouse antibody labeled by horseradish peroxidase was added. After another washing step, substrate solution was added and then absorbance was measured by spectrophotometer. The wells showed high reactivity were selected for the next step. (2) Sandwich reactivity using mAb 3C10 (anti PIVKA-II 17-24 antibody): Ten ug/mL of antibody to mouse Fc was added into the 96 well EIA plate, and anti mouse Fc antibody was coated onto the well surface. After blocking by a solution including Block Ace, 1:100 fold diluted supernatants of the hybridomas were then added to the wells. After washing step, heterophilic blocker reagent (HBR) was added to the wells to cap the remaining reaction site of the anti mouse Fc antibody previously coated. After washing step, biotinylated anti PIVKA 17-24 monoclonal antibody (Clone #3C10) was added to the wells. After washing step, Avidine labeled by horseradish peroxidase was added. After another washing step, substrate solution was added and then absorbance was measured by spectrophotometer. The results were shown in the FIG. 2. Hybridomas showed absorbance more than 1 OD were picked up for the next step.

Establishment of Clones: Cloning of the hybridomas 6H6 hybridoma was conducted using a standard procedure as described in Sakaguchi et al., The Journal of Immunology 174 (2005), pages 4485-4494. Clones of 6H6 were then established.

Example 2

Characterization of the 6H6 Monoclonal Antibody Affinity

Fluorescence correlation spectroscopy (FCS) was used to determine the $K_d$s of mAb 6H6 and PIVKA-II peptide (1-13), mAb 6H6 and Prothrombin peptide (1-13). FCS is a solution phase, single molecule level fluorescence technique that can measure the diffusion coefficient of fluorescent molecules. Large difference in the molecular mass of the free and antibody bound Alexa488-peptide results in a substantial change in diffusion coefficient, which in turn can be used to monitor the peptide and antibody interactions.

The sequence of the PIVKA-II peptide (1-13) was Alexa488-CANTFLEEVRKGNL (SEQ ID NO: 19) and the sequence of prothrombin peptide (1-13) was Alexa488-CANTFLE*E*VRKGNL (SEQ ID NO: 20). The concentration of labeled peptide was determined by absorption in a 1 cm cuvette using $\Sigma_{495}=71000$ $M^{-1}$ $cm^{-1}$. The concentration of mAb 6H6 was determined using $\Sigma_{280}=218000$ $M^{-1}$ $cm^{-1}$. The FCS experiments were performed using a dual-channel fluorescence correlation spectrometer ALBA (ISS, Champaign, Ill.) integrated with an inverted Nikon Eclipse TE300 fluorescence microscope (Nikon InsTech Co., Ltd., Kanagawa, Japan). Detailed information is described in S. Y. Tetin et al. (2006), "Interactions of two monoclonal antibodies with BNP: high resolution epitope mapping using fluorescence correlation spectroscopy." *Biochemistry* 45(47): 14155-65). The equilibrium dissociation constants ($K_d$) of the peptides and their antibody were measured in direct binding experiments by monitoring changes in autocorrelation curves of fluorescently labeled peptide in the presence of mAb 6H6. The Alexa-488 labeled peptide was kept at 2 nM, while the antibodies concentration incrementally increased from the sub-nanomolar to micromolar in the series of 15 samples. The fraction of antibody bound peptide was calculated from each autocorrelation curve using a two component-fitting model. The fitting routine and calculation of $K_d$ are described in S.Y Tetin et al. (2006).

Figure 3:
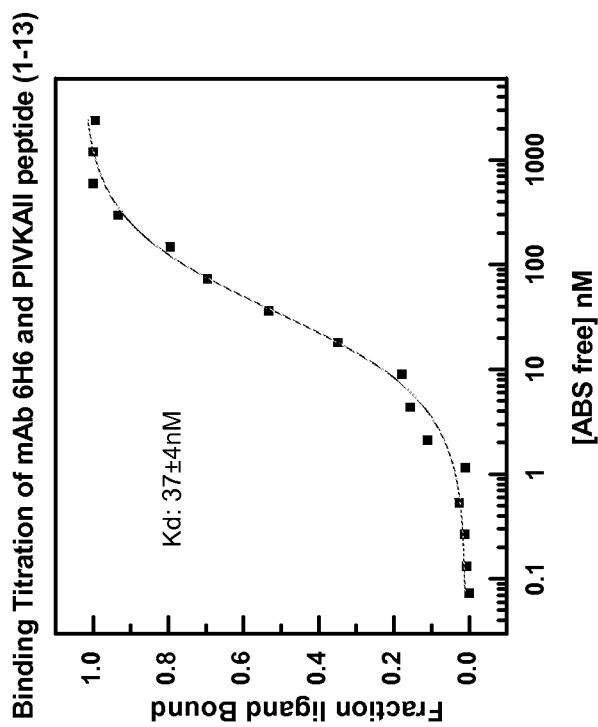
FIG. 3 shows the binding curve of mAb 6H6 (anti-PIVKA-II 1-13) and an Alexa488 labeled PIVKA-II peptide (1-13), showing a $K_d$ of mAb 6H6 for the PIVKA-II 1-13 peptide of 37±4 nM.
Figure 4:
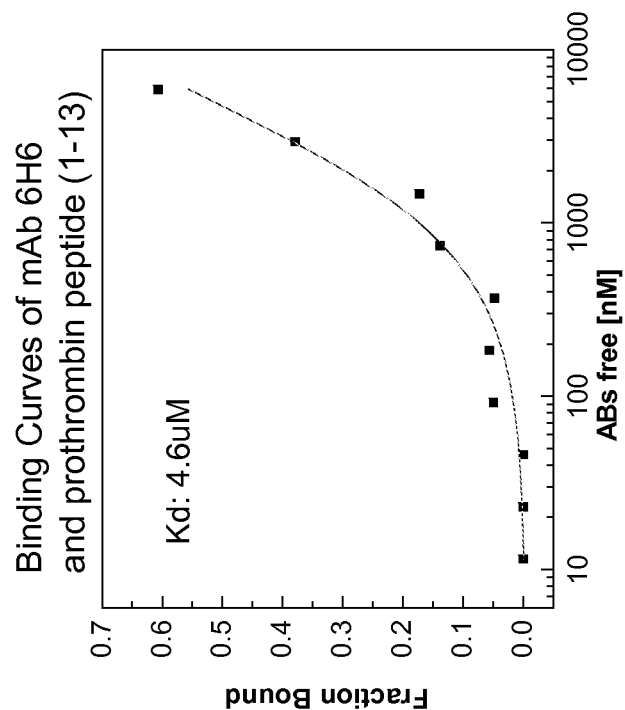
FIG. 4 shows the binding curve of mAb 6H6 and an Alexa488 labeled prothrombin peptide (1-13), showing a $K_d$ of the 6H6 mAb for the prothrombin peptide of 4.6±0.5 04.

All binding measurements were performed in 10 mM HEPES buffer, pH 7.4, containing 0.15M NaCl, 3 mM EDTA, and 0.005% surfactant P20. FIG. 3 shows the binding curve of mAb 6H6 and Alexa488-PIVKA-II peptide. The $K_d$ of mAb 6H6 for the PIVKA-II peptide is 37±4 nM. FIG. 4 shows the binding curve of mAb 6H6 and Alexa488-prothrombin peptide (1-13). Each data point on the curve was extracted from the fit of each autocorrelation curve (data not shown). The $K_d$ of the 6H6 mAb and the prothrombin peptide is 4.6±0.5 uM.

Labeling of PIVKA-II Peptide Cys1-13: To prepare the Alexa 488 PIVKA-II peptide (1-13), 6 mg of PIVKA-II (cys 1-13) was weighed into a 4 mL glass vial and dissolved in 2 mL of 50 mM MES pH 6.2, to this solution was added 1 mg of Alexa Fluor 488 malimide in 0.2 mL of DMF (i.e., dimethylformide). The mixture was incubated for 2 hrs at room temperature. The Alexa488 PIVKA-II peptide (1-13) was purified on a Phenomenex Luna 10 u, C18(2) 250×50 mm column (Phenomenex, Torrance, Calif.) using a gradient of acetonitrile water (10-40%) for 60 minutes. The pure fraction of the peak was pooled and lyophilized to obtain 0.6 mg of the dry powder. The concentration of labeled peptide was determined by absorption in 1 cm cuvette using E495=71000 M-1 cm$^{-1}$.

Example 3

Use of 6H6 in Immunoassay Automated Immunoassay

The hybridoma was cultured in serum free media. Antibodies in the culture supernatant were purified with a Protein A column. The purified 3C10 PIVKA-II specific monoclonal antibodies were coated to the magnetic microparticles. (A carboxyl group was attached to the surface of the microparticles (Abbott Laboratories, IL) with a covalent bond using 1-Ethyl-3-[3-dimethylaminopropyl]carbodiimide hydrochloride (EDC).) The coated microparticles were dispersed into the buffer solution, which included bovine serum albumin (BSA to make reagent A.

Acridinium conjugates were made from the 6H6 monoclonal antibody described above. The antibodies were labeled using N-hydroxysuccinimide (NHS) activated acridinium ester (Abbott Laboratories, IL). The labeled antibody was diluted into the buffer containing BSA to make Reagent B was prepared. Buffer solution including Triton X-100 was prepared as Reagent C. The immunoassay was automatically conducted with the following procedures utilized with the automated immunoassay system of ARCHITECT i2000 (Abbott Laboratories, IL). In particular, 50 uL of Reagent A and 50 uL of reagent C were mixed with 50 uL of sample. The mixture was incubated at 37° C. for 18 minutes to allow binding of antibody coated on the magnetic microparticles and reactive substance (PIVKA-II) in the sample. Magnetic microparticles were attracted by a magnet and then the residual solutions were removed. The magnetic microparticles were washed by phosphate buffered saline (PBS) so that impurities nonspecifically bound on the magnetic microparticle surface were removed. Fifty uL of Reagent B was then added to the microparticle and then the complex of (antibody coated magnetic microparticle)—(PIVKA-II in sample)—(acridinium labeled antibody) was formed. After a washing step by PBS, peroxide was added in the alkaline condition, and then acridinium ester produced a luminescent signal that was detected by a photo multiplier tube (PMT).

Figure 2:
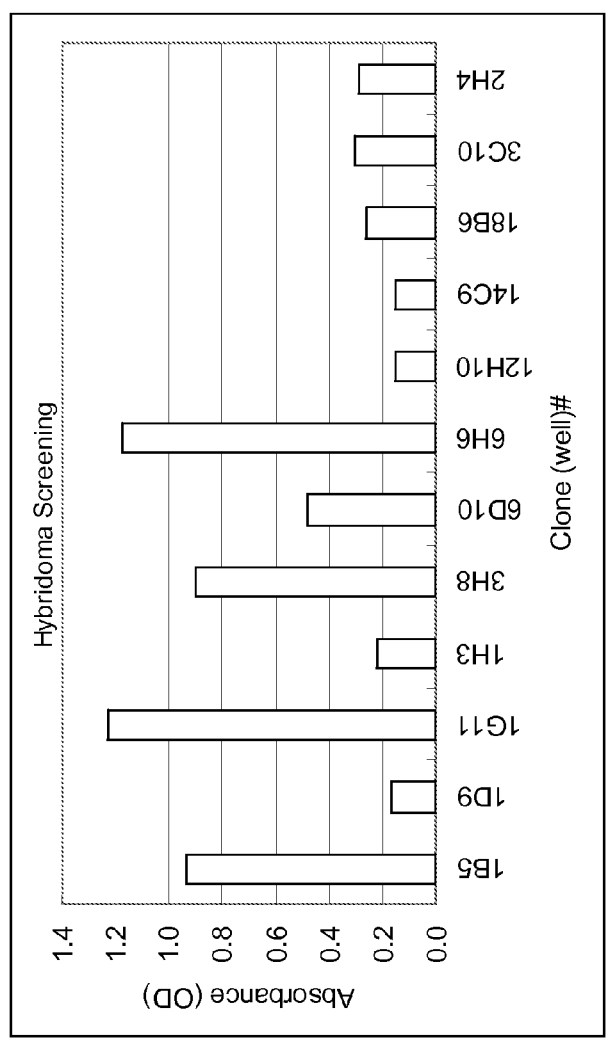
FIG. 2 is a bar graph of the results of hybridoma screening using sandwich reactivity using mAb 3C10 (anti-PIVKA-II 17-24).
Figure 5A:
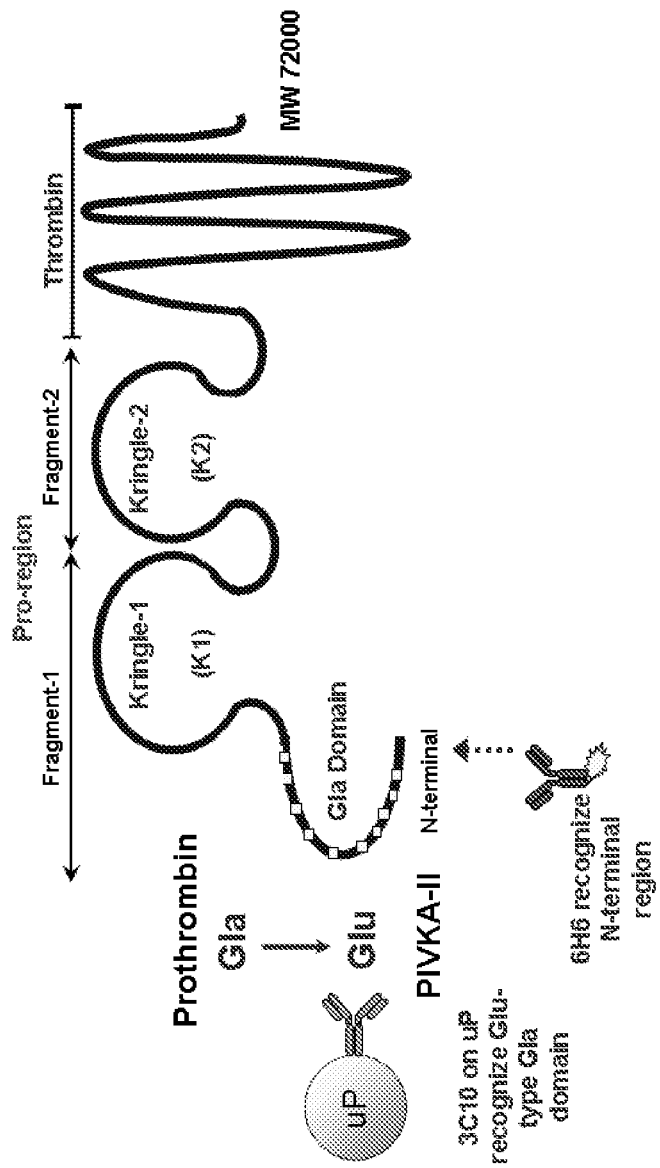
FIG. 5A is a schematic diagram of the human PIVKA II molecule showing sites of antibody reactivity.
Figure 5B:
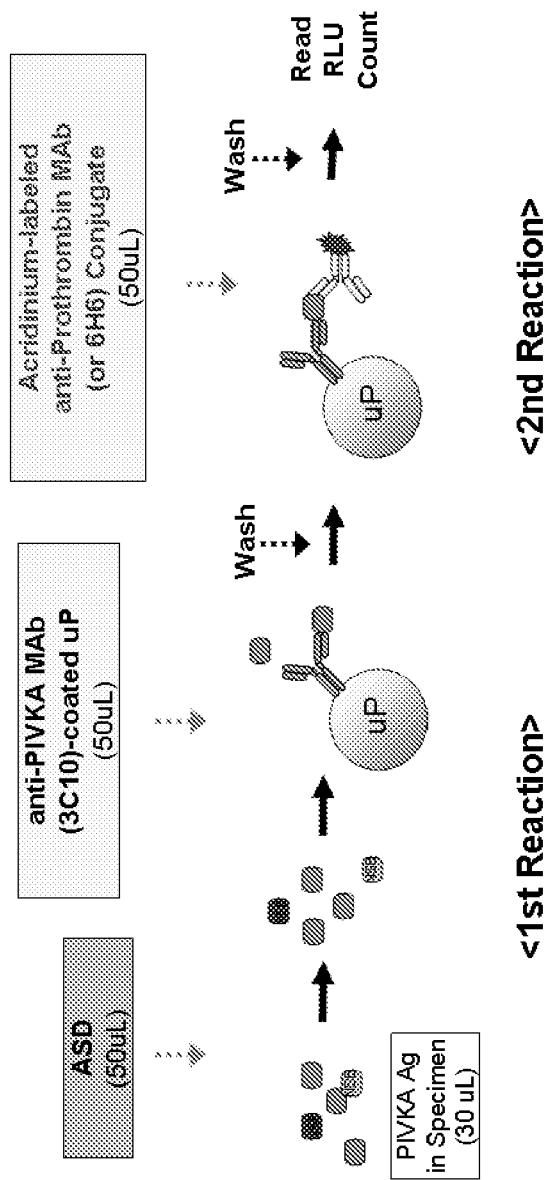
FIG. 5B is a schematic diagram of an automated immunoassay format using mAb 6H6.

PIVKA-II solution was tested with the Architect immunoassay using the 4 antibodies coated on the magnetic microparticles (FIG. 2). Clone 3C10 showed the strongest reactivity to the PIVKA-II antigen. These results indicated that 3C10 antibody showed high specificity for PIVKA-II and was highly reactive with PIVKA-II. The assay is calibrated using 6 calibrators with concentrations of 0 to 30000 mAU/mL PIVKA in a phosphate buffer containing BSA and anti-microbial agents at pH 7.4. A diagram of the human PIVKA-II molecule is shown in FIG. 5A with sites of antibody reactivity. A diagram of the assay format is shown is FIG. 5B.

Figure 6:
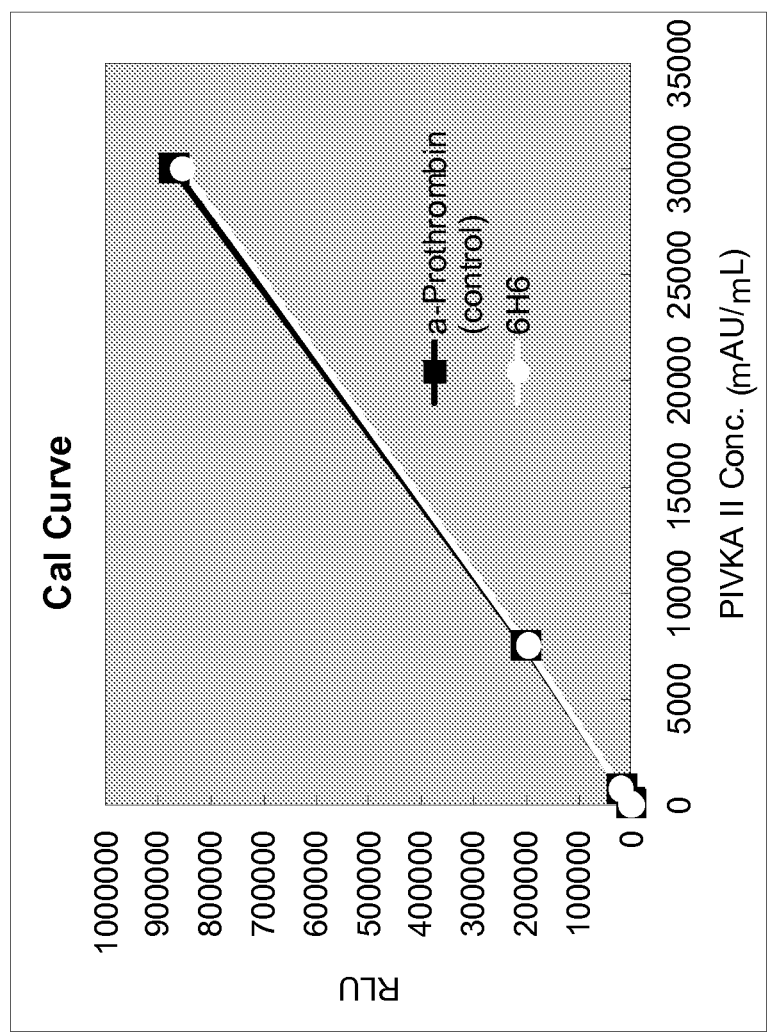
FIG. 6 is a graph of RLU (relative light units) values for each of six PIVKA-II calibrators used to measure performance of the control conjugate (MAC1-18) and the 6H6 conjugate, according to the assay format show in FIG. 5.

Evaluation of Assay Performance: The six calibrators were assayed in replicates of 5 and the mean RLU (relative light units) values for each calibrator using the control conjugate react to human prothrombin (Abbott Japan, Tokyo, Japan) and the 6H6 conjugate were compared in Table B and as shown in FIG. 6. Both conjugates gave good response in the assay.

TABLE B

| Calibrator | PIVKA Value | Anti-prothrombin (control) RLU | Anti PIVKA-II 1-13 (6H6) RLU |
|---|---|---|---|
| A | 0 mAU/mL | 190 | 547 |
| B | 20 mAU/mL | 683 | 1142 |
| C | 100 mAU/mL | 2596 | 2970 |
| D | 750 mAU/mL | 19034 | 19034 |
| E | 7500 mAU/mL | 203782 | 198142 |
| F | 30000 mAU/mL | 870813 | 854921 |

Figure 7:
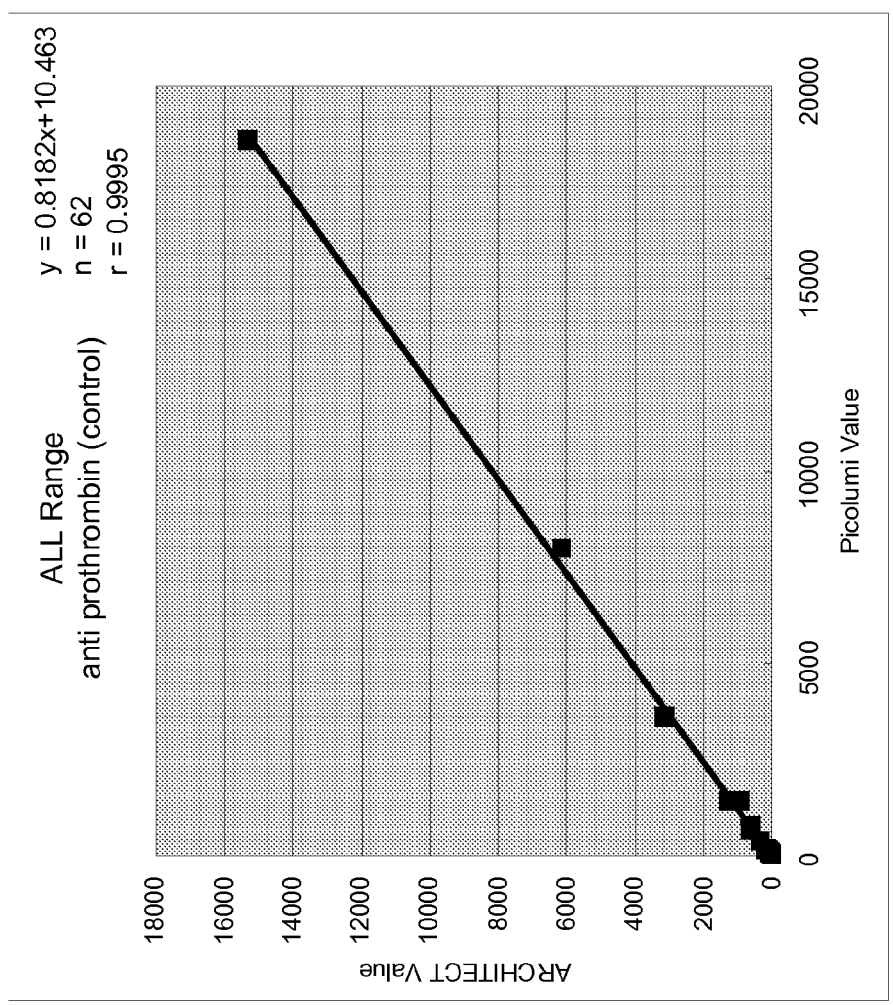
FIG. 7 is a graph of the correlation of assay results using MAC1-18 versus Picolumi across a Picolumi value range of 0-20000 mAU/mL.
Figure 8:
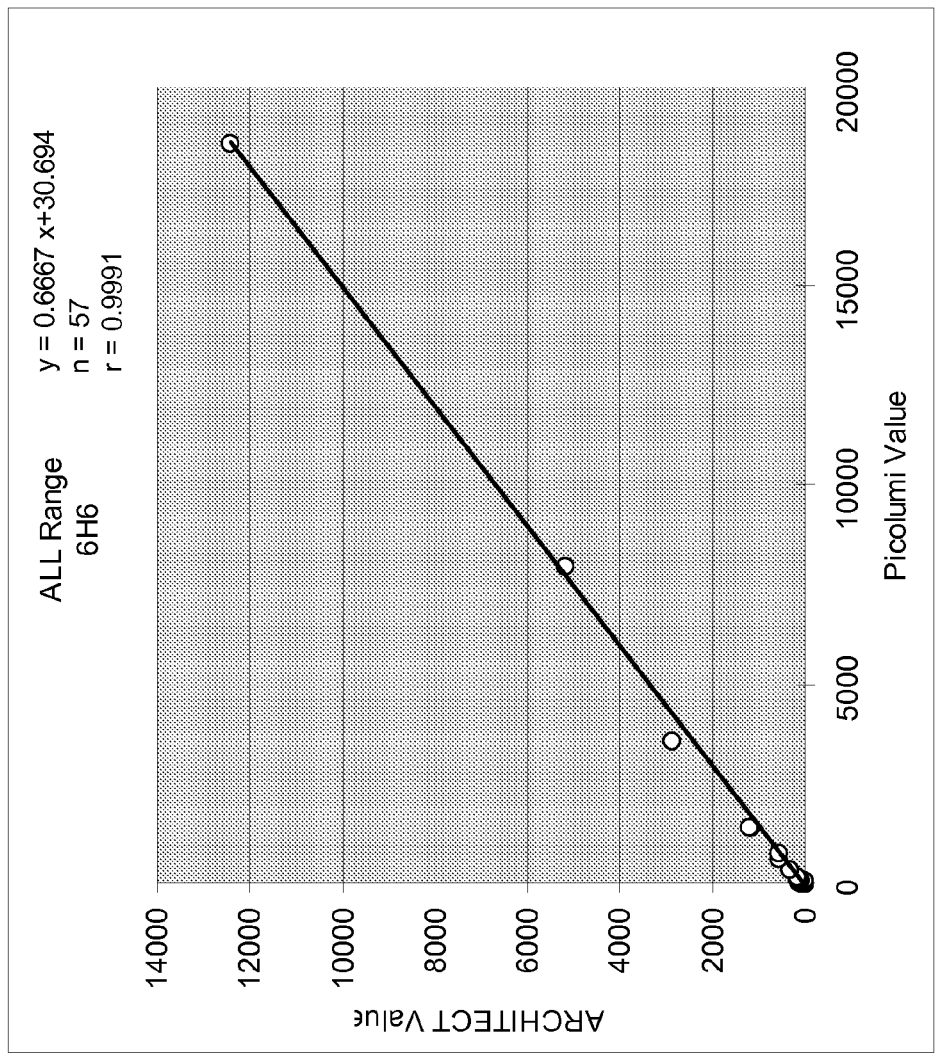
FIG. 8 is a graph of the correlation of assay results using 6H6 versus Picolumi across a Picolumi value range of 0-20000 mAU/mL.
Figure 9:
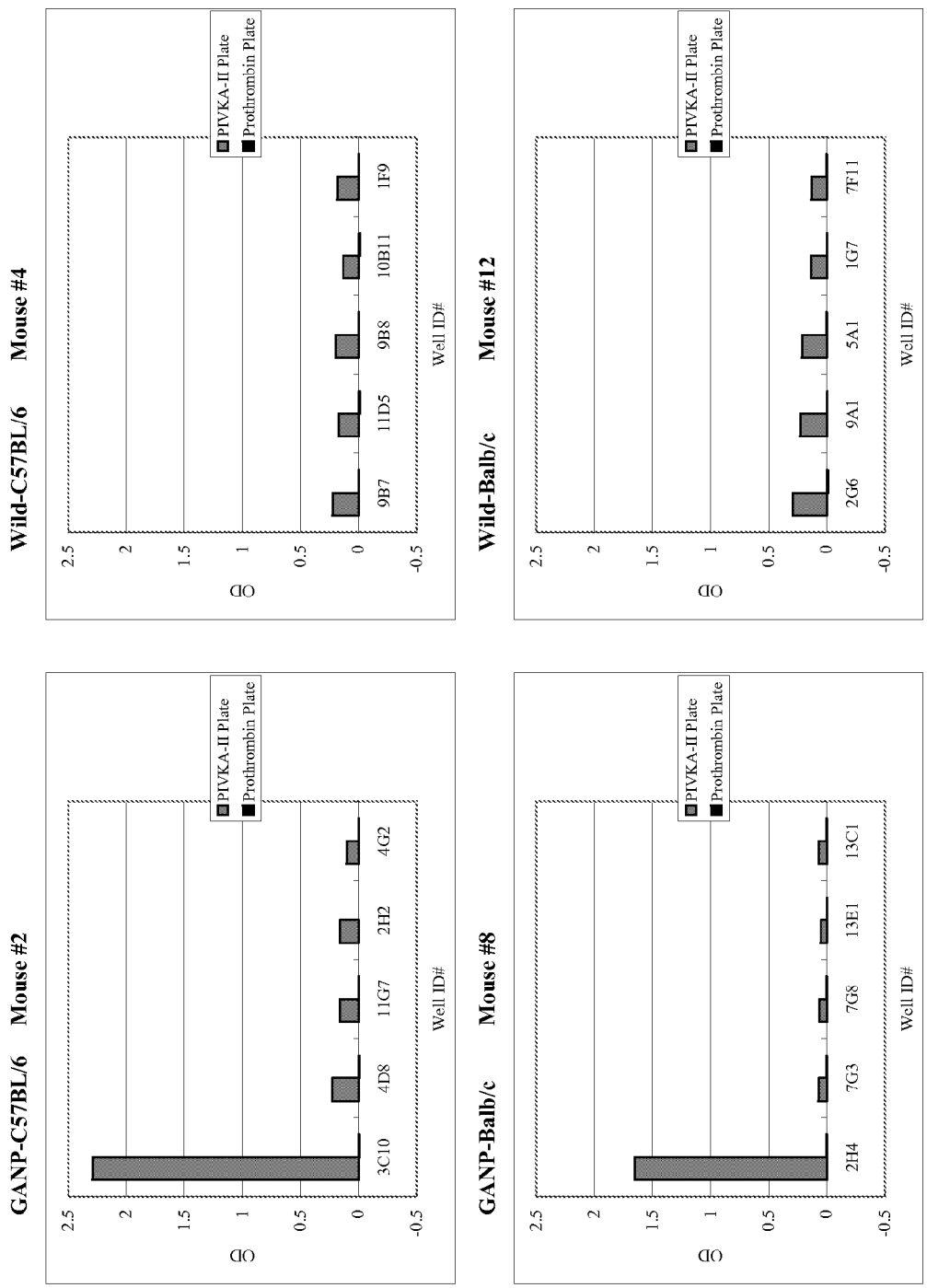
FIG. 9 illustrates the reactivity to PIVKA-II and Prothrombin in connection with the top five selected hybridomas in each group, showing reactivity of hybridomas from GANP transgenic mice or wild type mice to 35 PIVKA-II and Prothrombin.

The results from the two ARCHITECT PIVKA-II assays were compared to the results from a commercial PIVKA-II assay (Picolumi, EISAI, Japan), which uses a polyclonal anti-human prothrombin conjugate. Samples from apparently healthy persons (ProMedDx LLC, Norton, Mass.) and samples from patients with hepatocellular carcinoma (Clinical Research Center of Cape Cod, West Yarmouth, Mass.) were used. The correlation for both assay formats versus Picolumi is shown in FIGS. 7-8. These results demonstrate the ability of these assays to detect PIVKA-II in human serum.

Example 4

Development of 3C10 Cell Line

Design of immunogen: Seventeen mer peptides in the PIVKA-II specific region of PIVKA-II 13-27 were selected as immunogens. The 15 mer peptide in PIVKA-II had six decarboxylated amino acids of Glutamic acid, and prothrombin (factor-II) had six carboxylated glutamic acid (GLA) in the 15 mer peptide. The PIVKA-II specific 15 mer peptide, with a linker at the N-terminus wherein the linker was x-LERECVEETCSYEEA (SEQ ID NO: 21; disulfide bond between two cysteine)(x=epsilon-aminocaproic acid), conjugated with keyhole limpet hemocyanin (KLH) was designed as the immunogen. Synthesis of the peptide and conjugation to the KLH was conducted with a standard method. The N-terminal region of the peptide was bound to the KLH. Immunization: Peptide KLH was used to immunize wild type Balb/c, wild type C57BL/6 mice, germinal center-associated DNA primase (GANP) transgenic Balb/c mice, and GANP transgenic C57BL/6 mice. The method of GANP transgenic mice production and method of immunization were followed in accordance with the method described in Sakaguchi et al., *The Journal of Immunology* 174 (2005), pages 4485-4494. Reactivity determination to PIVKA-II and Prothrombin: PIVKA-II antigen was prepared by heating dried prothrombin powder (Sigma F5132) at 110° C. for 8 hours. (See Bajaj et al. *J. Biol. Chem.* (1982 Apr. 10), 257(7), pages 3726-31.)

After more than 8 weeks from immunization, mouse serum was bled and reactivity to PIVKA-II and reactivity to prothrombin were determined using the following procedures: Five ug/mL of PIVKA-II or 5 ug/mL of Prothrombin were added into the 96 wells of an Enzyme Immunoassay (EIA) plate, and PIVKA-II or prothrombin was coated onto the well surface. Mouse serum was diluted and then added to the wells. After a washing step, anti-mouse antibody labeled by horseradish peroxidase (HRP) was added. After another washing step, substrate solution was added, and then absorbance was measured by spectrophotometer. Mice that showed the highest reactivity to PIVKA-II and the lowest reactivity to Prothrombin in each group were selected for the next step.

Fusion: Spleen cells from the 4 mice selected from each group of wild type Balb/c, wild type C57BL/6, GANP transgenic Balb/c, and GANP transgenic C57BL/6 were fused to myeloma cells with a standard method as described in Sakaguchi et al., *The Journal of Immunology* 174 (2005), pages 4485-4494. The hybridoma cells were diluted by a limiting dilution method, and then the culture supernatant was used for the screening of the hybridomas.

Screening of Hybridoma: Screening of the hybridomas was performed by use of the following procedures: One ug/mL of PIVKA-II or 5 ug/mL of Prothrombin was added into the 96 well EIA plate, and PIVKA-II or Prothrombin was coated onto the well surface. After blocking by a solution including Block Ace, supernatants of the hybridomas were then added to the wells. After a washing step, anti-mouse antibody labeled by horseradish peroxidase was added. After another washing step, substrate solution was added and then absorbance was measured by spectrophotometer. The top 5 hybridomas in each group were selected by the following criteria: (1) no reactivity to prothrombin and then (2) top 5 reactivity to PIVKA-II No hybridomas that were obtained from wild type mice reacted with PIVKA-II strongly. Hybridoma #3C10 from GANP transgenic C57BL/6 showed strong reactivity to PIVKA-II and no reactivity to prothrombin. It was thought that the method using GANP transgenic mouse with PIVKA-II peptide as immunogen could produce clones that produced antibody which had higher reactivity to PIVKA-II than wild mouse as well as no reactivity to the prothrombin.

Establishment of Clones: Cloning of hybridomas #3C10 and #2H4 were conducted using a standard procedure as described in Sakaguchi et. al., *The Journal of Immunology* 174 (2005), pages 4485-4494. Clones of 3C10 and 2H4 were then established. Using the same procedures of fusion, screening of hybridomas and establishment of clones as described above for one of each group of GANP transgenic Balb/c and GANP transgenic C57BL/6 mice, clone #12D6 from GANP transgenic C57BL/6 mouse and clone #7B10 from GANP transgenic Balb/c mouse were established. These clones had strong reactivity to PIVKA-II and no reactivity to Prothrombin.

Example 5

Hybridoma Screening with Automated Immunoassay Using the Architect System

Figure 10:
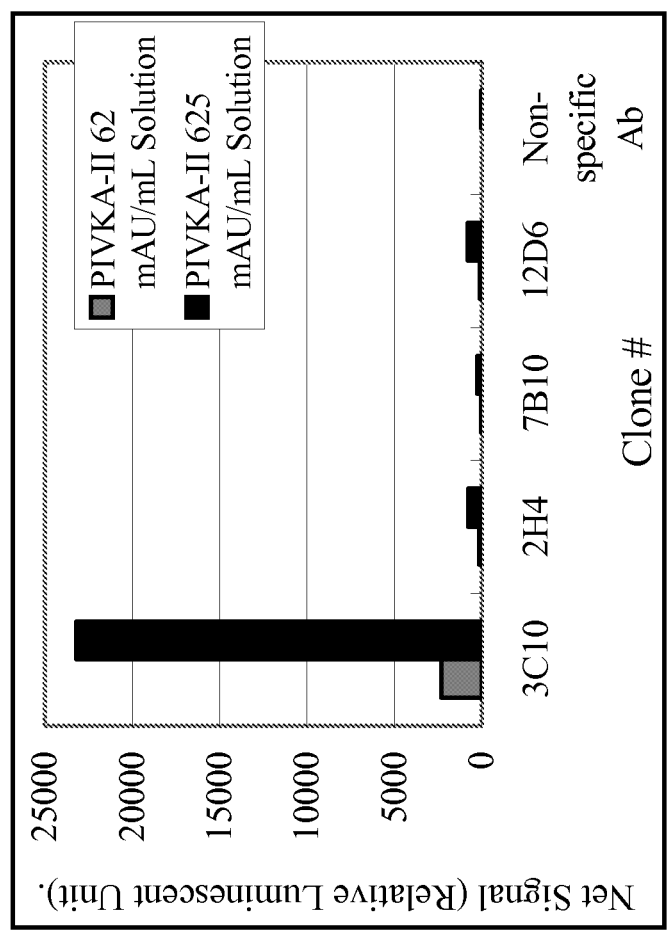
FIG. 10 shows the signals of several antibodies, showing strong reactivity of Mab 3C10 to the PIVKA-II antigen.

Automated Immunoassay: Each hybridoma was cultured in to serum free media. Antibodies in the culture supernatant were purified with a Protein A column. The antibodies were coated to the magnetic microparticles. (A carboxyl group was attached to the surface of the microparticles (Abbott Laboratories, IL) with a covalent bond using 1-Ethyl-3-(3-dimethylaminopropyl)carbodiimide hydrochloride (EDC).) The coated microparticles were dispersed into the buffer solution, which included bovine serum albumin (BSA) and then Reagent A was prepared. Anti-Prothrombin antibody (code #PA150) from Hyphen Biomed (France) was labeled by N-hydroxysuccinimide (NHS) activated acridinium ester (Abbott Laboratories, IL). The labeled antibody was diluted into the buffer containing BSA, and then Reagent B was prepared. Buffer solution including Triton X-100 was prepared as Reagent C. The immunoassay was automatically conducted with the following procedures utilized with the automated immunoassay system of ARCHITECT i2000 (Abbott Laboratories, Abbott Park, Ill.). In particular, 50 uL of Reagent A and 50 uL of reagent C were mixed with 50 uL of sample. The mixture was incubated at 37° C. for 18 minutes to allow binding of antibody coated on the magnetic microparticles and reactive substance (PIVKA-II) in the sample. Magnetic microparticles were attracted by a magnet and then the residual solutions were removed. The magnetic microparticles were washed by phosphate buffered saline (PBS) so that impurities nonspecifically bound on the magnetic microparticle surface were removed. Fifty uL of Reagent B was then added to the microparticle and then the complex of (antibody coated magnetic microparticle)—(PIVKA-II in sample)—(acridinium labeled antibody) was formed. After a washing step by PBS, peroxide was added in the alkaline condition, and then acridinium ester produced a luminescent signal that was detected by a photo multiplier tube (PMT). PIVKA-II solution was tested with the Architect immunoassay using the four antibodies coated on the magnetic microparticles (FIG. 10). Clone 3C10 showed the strongest reactivity to the PIVKA-II antigen. These results indicated that 3C10 antibody showed high specificity for PIVKA-II and was highly reactive with PIVKA-II.

Example 6

Figure 11:
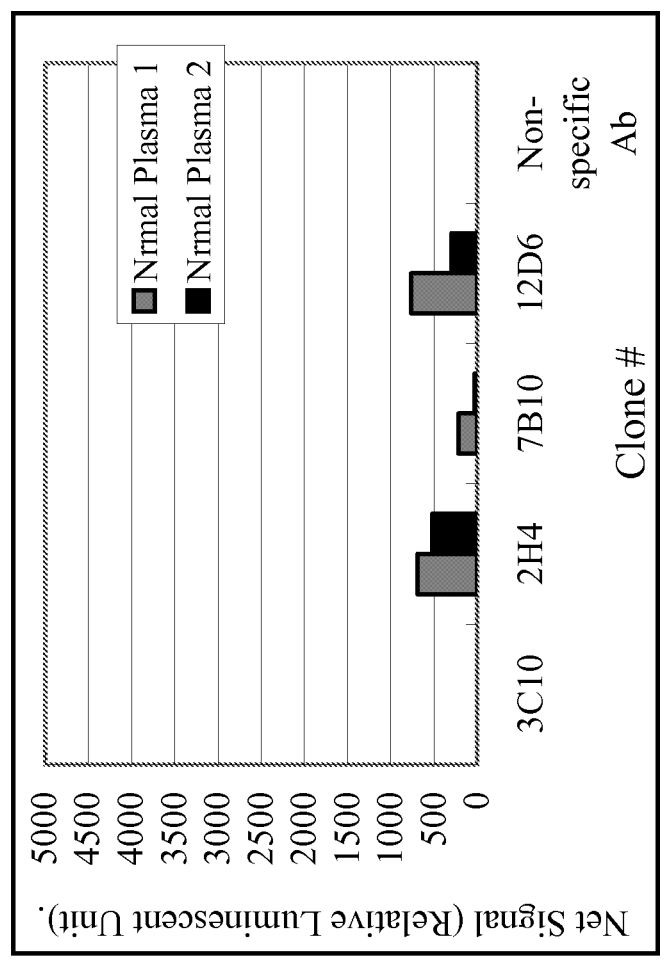
FIG. 11 shows the subtracted PIVKA-II signal and background in connection with the procedure noted in Example 6.

Reactivity of Clones 3C10, 2H4, 7B10 and 12D6 to Plasma Substances Using an Automated Immunoassay Two normal plasma specimens known to have the PIVKA-II value of 23 mAU/mL and 23.5 mAU/mL were tested with the Architect immunoassay using the 4 antibodies from clone #3C10, 2H4, 7B10, and 12D6 coated on the magnetic microparticles. Clone 3C10 and 7B10 showed no or little signal from the plasma (FIG. 11). This result indicated that 3C10 and 7B10 had no cross reactivity to the plasma substances including Factor II (Prothrombin), Factor IX, Factor X, Factor VII, Protein C, Protein S, and Protein Z. In particular, since Factor II is the precursor of PIVKA-II Factor HH and has a GLA domain that contains carboxylated glutamic acid, and these amino acids are absent in PIVKA-II, the antibody 3C10 is specific to these changes and does not recognize Factor II/prothrombin. Other coagulation factors such as Factor IX, Factor X and Factor VII also contain the GLA domain with a few amino acids being preferentially different (i.e., homologous proteins). Hence, the antibody 3C10 does not recognize any of these proteins although they are very similar in amino acid sequence to PIVKA-II.

Example 7

Characterization of the Antibodies a) Material and Methods:
Sequences of the peptides synthesized (SEQ ID NO: 22 and SEQ ID NO: 23):

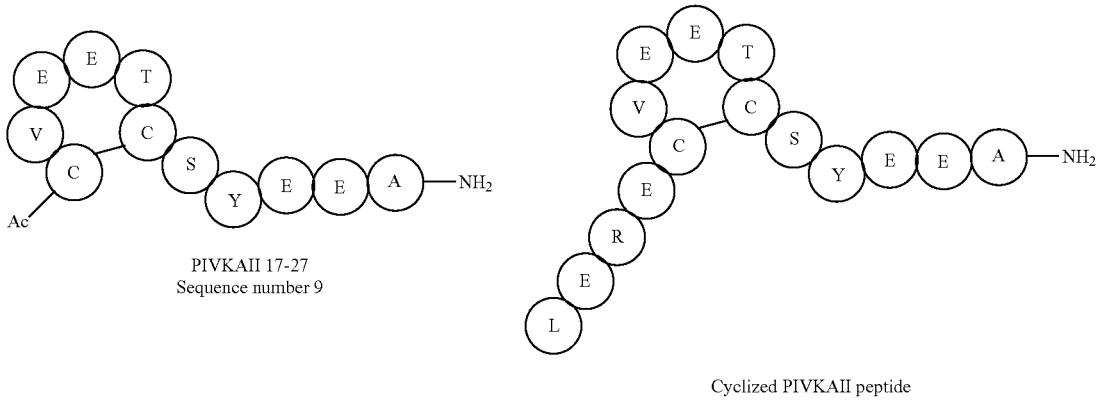

PIVKA-II 17-27 peptides synthesized to evaluate the epitope specificity of the length of the peptide were (SEQ ID NOS: 1-10 and 24, respectively, in order of appearance):

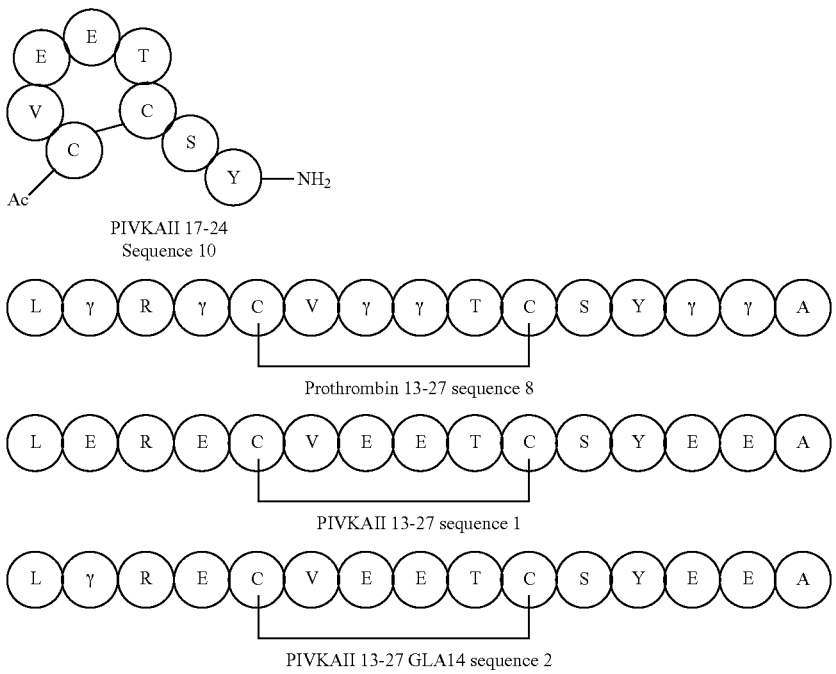

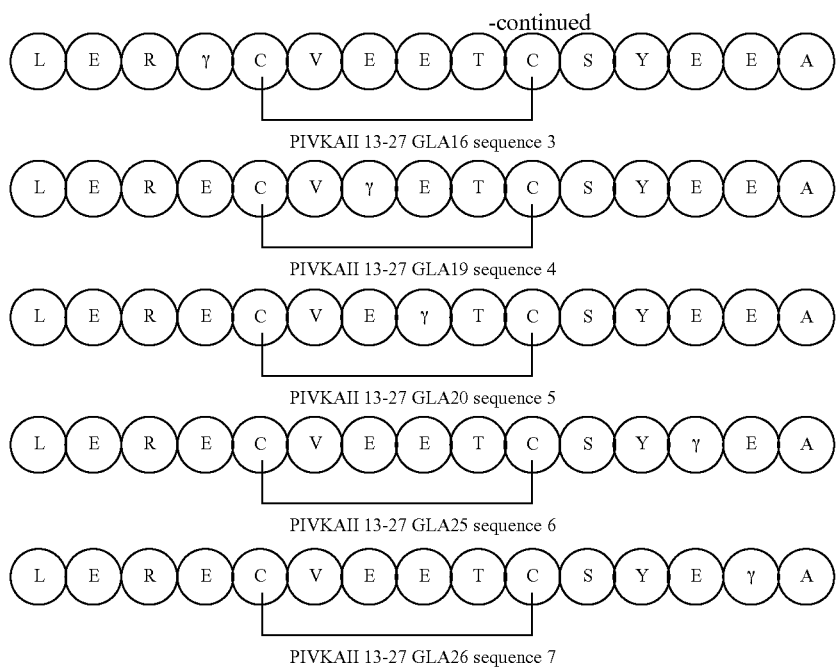

Homologous series of peptides (all cyclic peptides implying the di-sulphide formation; variable residues are shown in bold):

```
LERECMEEKCSFEEA  (13-27 Gla domain PIVKA IX; SEQ ID NO: 11)

LERECMEETCSYEEA  (13-27 Gla domain PIVKA Factor X; SEQ ID NO: 12)

LERECKEEQCSFEEA  (13-27 Gla domain PIVKA Factor VII; SEQ ID NO: 13)

LERECIEEICDFEEA  (13-27 Gla domain PIVKA Protein C; SEQ ID NO: 14)

LERECIEELCNKEEA  (13-27 Gla domain PIVKA Protein S; SEQ ID NO: 15)

LEKECYEEICVYEEA  (13-27 Gla domain PIVKA Protein Z; SEQ ID NO: 16)

LERECVEETCSYEEA  (13-27 PIVKA-II SEQUENCE; SEQ ID NO: 17)
```

Sequence homology analysis using Biology workbench: The GLA domain of prothrombin has sequence homology with other co-aggulation proteins. The protein sequence of Prothrombin, Protein Z, Protein S, Protein C, Factor X and Factor IX were retrieved from the Swiss-pro database and the GLA domain of these proteins was copied and fed into Biology workbench software (San Diego Supercomputer Center (SDSC), La Jolla, Calif.) for sequence alignment. The sequence alignment showed homology in the region of interest (i.e., 13 to 27) embedded in the GLA region of Prothrombin.

Peptide Synthesis: Peptides were synthesized using commercially available Fmoc protected amino acids on a Pioneer synthesizer from ABI (Foster City, Calif.) or using a CS Bio synthesizer (Menlo Park, Calif.). The amino acids were activated with coupling reagents such as PyBOP (i.e., benzotriazol-1-ylosytripyrrolidinophsphonium hexafluorophosphate) or PyAOP (i.e., 7-azabenzotriazol-1-yloxy-tris-(pyrrolidono) phosphonium hexafluorophosphate) The Fmoc protection was removed on the instrument, and the N-terminal amine was not capped. The peptides were cleaved using 2.5% water, 2.5% tri-isopropyl silane, and 95% TFA (i.e., trifluoroacetic acid) reagent mixture for 1-2 hrs at room temperature. The cleaved peptide was precipitated with ether, dissolved in 50% aq. acetonitrile, and lyophilized to obtain the required peptide. This is the general procedure that was utilized for peptide synthesis for sequences #1 to 20. (See below.)

Cyclization of PIVKA-II: 50 mg diAcm PIVKA-II peptide (13-27) was mixed in 20 mL of acetic acid ("AcOH"):$H_2O$ mixture, (1:1 v/v). Two mL of 1N HCl was added followed by addition of 30 milligrams of iodine as a solution in 1 mL of methanol ("MeOH"):AcOH (1:1 v/v) (Greg Fields ed., *Methods in Enzymology*, Vol. 289, pp. 198-221, 1997). The reaction mixture was stirred for 45 minutes under dark conditions. The reaction mixture was a clear brown solution without any suspended particles.

After 45 minutes, the reaction was quenched by adding a 10% solution of ascorbic acid. In particular, approximately 100 mg of an ascorbic acid solution (i.e., approximately 10 mL) was added (which is commercially available from Aldrich, Milwaukee, Wis.) drop-wise until the solution was clear. The solution was diluted 4 times with water and purified by preparative HPLC. A Phenomenex Luna 10 u, C18 (2) 250× 50 mm column (Phenomenex, Torrance, Calif.) was used for purification, using a gradient of acetonitrile water (10-40%) for 60 minutes. The peptide was collected in fractions as the peak rose, and the fractions were checked by HPLC. The fractions with the highest purity (i.e., >98%) were pooled and lyophilized. One hundred and ten mgs of cyclized cyclized PIVKA-II peptide (13-27) were obtained.

Labeling of PIVKA-II Peptide: To prepare the Alexa 488 PIVKA-II peptide (13-27), 4 mg of cyclized PIVKA-II (13-27) were weighed into a 4 mL glass vial and treated with 2 mg of Alexa Fluor 488 TFP active ester in 1 mL of DMF (i.e., dimethylformide). To this mixture was added 0.2 mL of DIEA (i.e., diisopropylethylamine) and the mixture was incubated for 2 hrs. The Alexa488 PIVKA-II peptide (13-27) was purified on a Phenomenex Luna 10 u, C18(2) 250×50 min column (Phenomenex, Torrance, Calif.) using a gradient of acetonitrile water (10-40%) for 60 minutes. The pure fraction of the peak was pooled and lyophilized to obtain 0.6 mg of the dry powder. The concentration of labeled peptide was determined by absorption in 1 cm cuvette using E495=71000 $M^{-1}$ $cm^{-1}$.

Labeling of the Antibody: Anti-PIVKA-II mAb 3C10 was selectively labeled with Black Hole Quencher (BHQ, Biosearch Technologies, Inc. Novato, Calif.). Purification and labeling procedures were provided by the vendor. The unlabeled BHQ-10s were removed on a G-25 column equilibrated with PBS. The concentrations of the labeled mAbs were determined using $\Sigma_{280}$=218000 $M^{-1}$ $cm^{-1}$, with corrections for contributions from BHQ (218000 $M^{-1}$ $cm^{-1}$). The molar incorporation ratio (I.R. dye/protein) was calculated based on the concentration of the protein and chromophore. The I.R. for mAb 3C10 is 2.3.

Fluorescence-based methods: Fluorescence anisotropy and förster resonance energy transfer (FRET) were used to determine the dissociation constants of Alexa-488 labeled PIVKA-II Gla domain peptide (13-27) and monoclonal antibodies developed against this peptide. In particular, fluorescence correlation spectroscopy (FCS) was used to compare the binding strength of the Gla-substituted PIVKA-II peptide (13-27) mutants and identify the epitopic Gla residues of the PIVKA-II peptide (13-27). FCS is a solution phase, single molecule level fluorescence technique that can measure the diffusion coefficient of fluorescent molecule. Large differences in the molecular masses of the free and antibody bound Alexa488-PIVKA-II (13-27) results in a substantial change in diffusion coefficient, which in turn can be used to monitor the analyte and antibody interactions.

Instrumentation: All equilibrium fluorescence measurements were performed on an SLM 8100 photon counting spectrofluorimeter (SLM; no longer in existence). For anisotropy measurement, samples were excited at 480 nm, and emission fluorescence signals were collected through a polarizer and a 530/30 nm interference filter. Anisotropy values for each sample were measured 5 times, and the average value was recorded. For fluorescence intensity measurements, samples were excited at 480 nm. Total emission fluorescence signals were collected through a 530/30 nm interference filter (polarizer removed to improve sensitivity). Total fluorescence signals for each sample were measured 5 times, and the average value was recorded. FSC experiments were performed using a dual-channel fluorescence correlation spectrometer ALBA (ISS, Champaign, Ill.) integrated with an inverted Nikon Eclipse TE300 fluorescence microscope (Nikon InsTech Co., Ltd., Kanagawa, Japan). Detailed information is described in Tetin et al., Biochemistry, 2006, 45:14155-65.

Determination of the Dissociation Constants: The equilibrium dissociation constants ($K_d$) of antigens (with the antibody of interest) were measured in direct binding experiments by monitoring changes in fluorescence anisotropy or fluorescence intensity. The Alexa-488 labeled antigen was kept at concentrations well below the $K_d$, while the antibodies' concentration incrementally increased from the picomolar range to sub-micromolar in the series of fifteen samples. Since there is no fluorescence intensity quenching of Alexa488-antigen when it binds to the antibody, the change in anisotropy is directly proportional to the fraction of antigen bound to antibody (Fb) as follows:

$$Fb(i) = \frac{A(i) - A\min}{A\max - A\min} \quad (1)$$

where $A_{(i)}$ is the anisotropy of Alexa488-antigen at each antibody concentration, $A_{min}$ is the anisotropy of Alexa488-antigen alone, and $A_{max}$ is the anisotropy of antibody bound Alexa488-antigen. The concentration of the unbound antibody binding sites [ABS free] can be calculated from the following formula:

$$[ABS_{free}]=[ABS_{total}]-[T_{total}] \times Fb \quad (2)$$

The binding data were then fitted with the simple binding model to calculate the equilibrium dissociation constant:

$$K_d: Fb = \frac{[ABS_{free}]}{K_d + [ABS_{free}]} \quad (3)$$

For high affinity monoclonal antibody 3C10 (mAb 3C10), a lower concentration of Alexa488-antigen (50 μM) is required for the binding measurement, which is below the sensitivity of anisotropy measurement. A different approach is therefore used. In particular, by introducing a Black-hole quencher (none fluorescent chromophore) onto the mAb 3C10, the fluorescence intensity of Alexa488-antigen is quenched upon its binding to mAb 3C10. The quenching (Q) of fluorescence 5 intensity of the antigen ($I_i$) at each antibody concentration is calculated from equation 4.

$$Q = 1 - \frac{I_i}{I_{max}}, Q_{max} = 1 - \frac{I_{min}}{I_{max}} \quad (4)$$

where Imax is the fluorescence intensity of the antigen in the absence of antibody. Imin is the fluorescence intensity of the antigen at highest antibody concentration. Assuming that the value of Q/Qmax can be directly translated into the fraction of Alexa488-antigen bound to its monoclonal antibody, the concentration of the unbound antibody binding sites, $[ABS_{free}]$ can be calculated from the following formula:

$$[ABS_{free}]=[ABS_{total}]-[T_{total}] \times Q/Q_{max} \quad (5)$$

where $[ABS_{total}]$ and $[T_{total}]$ are the antibody binding sites and total concentrations of the Alexa488-peptide, respectively. The binding data were then fitted with the simple binding model to calculate the equilibrium dissociation constant.

$$K_d: Q = \frac{Q_{max} * [ABS_{free}]}{K_d + [ABS_{free}]} \quad (6)$$

Figure 12:
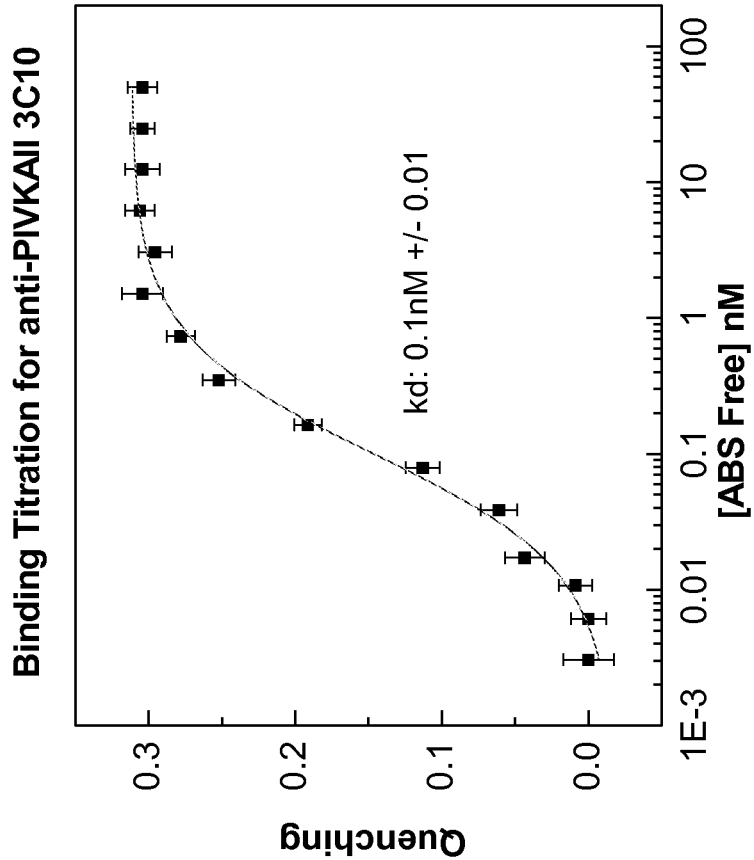
FIG. 12 illustrates the equilibrium dissociation constants ($K_d$) of antigens measured in direct binding experiments, in which Alexa-488 labeled PIVKA-II Gla domain peptide (13-27) was kept at 0.05 nM, while the concentration of BHQ-mAb varied from 50 nM to 0.0002 nM.
Figure 13:
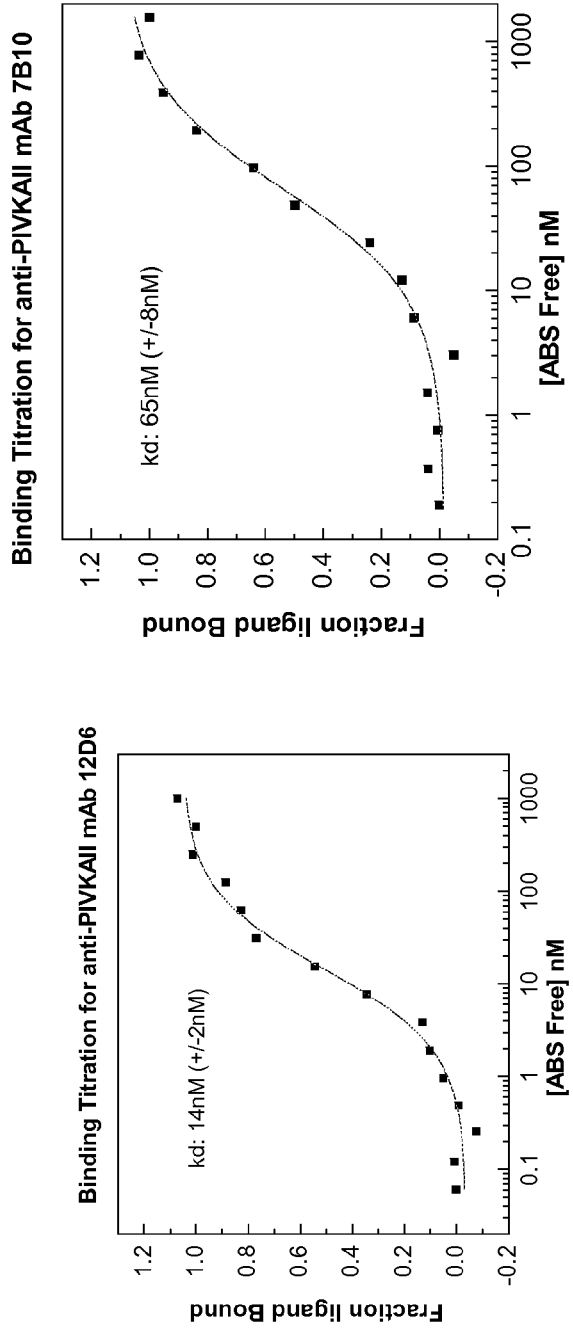
FIG. 13 illustrates the equilibrium dissociation constants ($K_d$) of antigens measured in direct binding experiments, in which Alexa-488 labeled PIVKA-II Gla domain peptide (13-27) was kept at 0.2 nM, while the concentration of mAbs varied from 1 pM to sub nano-molar.
Figure 14:
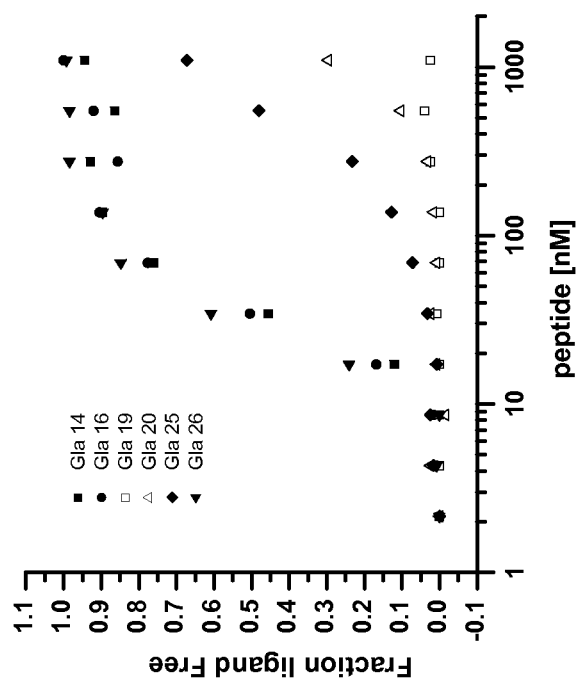
FIG. 14 illustrates FCS measurements of individual samples in which Alexa488-PIVKA-II peptide (13-27 cyc) was premixed with mAb 3C10 and various amounts of Glu-substituted peptide (Gla14, Gla 16, Gla 19, Gla 20, Gla 25, Gla26) were then added to the antigen-antibody complex.
Figure 15:
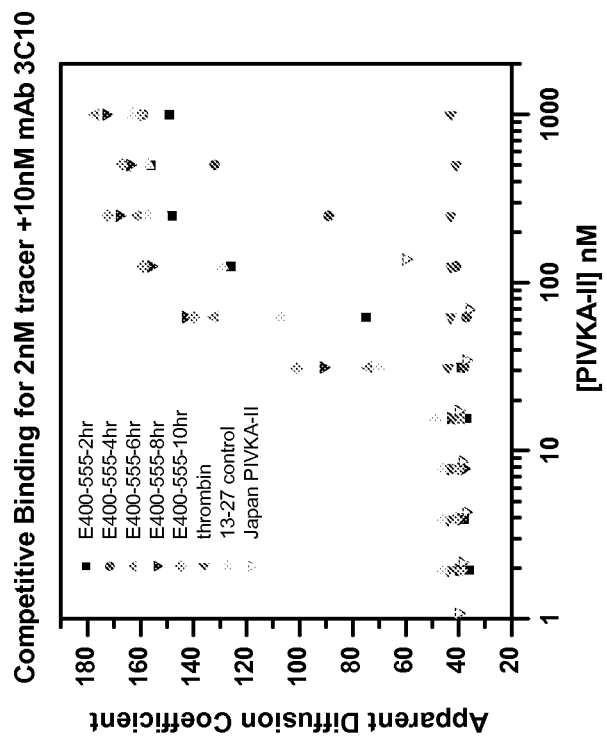
FIG. 15 illustrates additional FCS measurements of each sample in which Alexa488-PIVKA-II peptide (13-27 cyc) was premixed with mAb 3C10, and various amounts of PIVKA-II from different preparations were added to the antigen-antibody complex.
Figure 16:
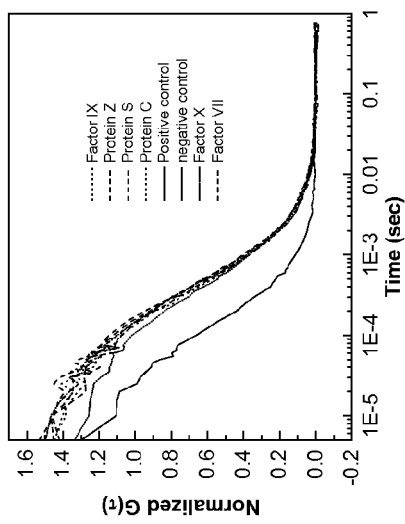
FIG. 16 illustrates the results obtained when competitive binding measurements of various PIVKA-II Gla domain (13-27) analogs with Alexa488-PIVKA-II (13-27) and mAb 3C10 were used to test cross-reactivity with mAb 3C10.

All binding measurements were performed in 10 mM HEPES buffer, pH 7.4, containing 0.15M NaCl, 3 mM EDTA, and 0.005% surfactant P20. The bind titration curves of Alexa-488 labeled PIVKA-II Gla domain peptide (13-27) and the mAbs are shown in FIGS. 12 and 13. The dissociation constants and changes in anisotropy of Alexa488-antigen upon its binding to mAbs are listed in Table C below:

TABLE C

|  | Kd (nM) | Anisotropy Changes |
|---|---|---|
| mAb 1B9 | 92 (+/−) 12 | 0.05−>0.17 |
| mAb 7B10 | 65 (+/−) 8 | 0.05−>0.16 |
| mAb 12D6 | 14 (+/−) 2 | 0.05−>0.14 |
| mAb 2H4 | 2 (+/−) 0.4 | 0.05−>0.17 |
| mAb 3C10 | 0.15 (+/−) 0.1 | 0.05−>0.095 |

Epitope Mapping By Fluorescence Correlation Spectroscopy: The competitive binding measurements of Glu-substituted peptide with Alexa488-PIVKA-II (13-27) and mAb 3C10 identified 10 specific Gla residues in the 13-27 region that play a critical role in epitope recognition for mAb 3010. The results showed that residues Gla 19, 20 and 25 are involved in epitope recognition for mAb 3C10, as replacement with Glu at each of those positions partially or completely eliminates the rec

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(6)
<223> OTHER INFORMATION: Cyclic
<220> FEATURE:
<223> OTHER INFORMATION: C-term NH2

<400> SEQUENCE: 3

Cys Val Glu Glu Thr Cys Ser Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4-carboxyglutamic acid
<220> FEATURE:
<221> NAME/KEY: MOD_RES
<222> LOCATION: (4)..(4)
<223> OTHER INFORMATION: 4-carboxyglutamic acid
<220> FEATURE:
<221> NAME/KEY: misc_feature
<222> LOCATION: (5)..(10)
<223> OTHER INFORMATION: Cyclic
<220> FEATURE:
<221> NAME/KEY: MOD_RES
<222> LOCATION: (7)..(8)
<223> OTHER INFORMATION: 4-carboxyglutamic acid
<220> FEATURE:
<221> NAME/KEY: MOD_RES
<222> LOCATION: (13)..(14)
<223> OTHER INFORMATION: 4-carboxyglutamic acid

<400> SEQUENCE: 4

Leu Glu Arg Glu Cys Val Glu Glu Thr Cys Ser Tyr Glu Glu Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(10)
<223> OTHER INFORMATION: Cyclic

<400> SEQUENCE: 5

Leu Glu Arg Glu Cys Val Glu Glu Thr Cys Ser Tyr Glu Glu Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: 4-carboxyglutamic acid
<220> FEATURE:
<221> NAME/KEY: misc_feature
<222> LOCATION: (5)..(10)
<223> OTHER INFORMATION: Cyclic

<400> SEQUENCE: 6

Leu Glu Arg Glu Cys Val Glu Glu Thr Cys Ser Tyr Glu Glu Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 4-carboxyglutamic acid
<220> FEATURE:
<221> NAME/KEY: misc_feature
<222> LOCATION: (5)..(10)
<223> OTHER INFORMATION: Cyclic

<400> SEQUENCE: 7

Leu Glu Arg Glu Cys Val Glu Glu Thr Cys Ser Tyr Glu Glu Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 4-carboxyglutamic acid
<220> FEATURE:
<221> NAME/KEY: misc_feature
<222> LOCATION: (5)..(10)
<223> OTHER INFORMATION: Cyclic

<400> SEQUENCE: 8

Leu Glu Arg Glu Cys Val Glu Glu Thr Cys Ser Tyr Glu Glu Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 4-carboxyglutamic acid
<220> FEATURE:
<221> NAME/KEY: misc_feature
<222> LOCATION: (5)..(10)
<223> OTHER INFORMATION: Cyclic

<400> SEQUENCE: 9

Leu Glu Arg Glu Cys Val Glu Glu Thr Cys Ser Tyr Glu Glu Ala
1               5                   10                  15
```

```
<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(10)
<223> OTHER INFORMATION: Cyclic
<220> FEATURE:
<221> NAME/KEY: MOD_RES
<222> LOCATION: (13)..(13)
<223> OTHER INFORMATION: 4-carboxyglutamic acid

<400> SEQUENCE: 10

Leu Glu Arg Glu Cys Val Glu Glu Thr Cys Ser Tyr Glu Glu Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Glu Arg Glu Cys Met Glu Glu Lys Cys Ser Phe Glu Glu Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu Arg Glu Cys Met Glu Glu Thr Cys Ser Tyr Glu Glu Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Glu Arg Glu Cys Lys Glu Glu Gln Cys Ser Phe Glu Glu Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Glu Arg Glu Cys Ile Glu Glu Ile Cys Asp Phe Glu Glu Ala
1               5                   10                  15

<210> SEQ ID NO 15
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Glu Arg Glu Cys Ile Glu Glu Leu Cys Asn Lys Glu Glu Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Glu Lys Glu Cys Tyr Glu Glu Ile Cys Val Tyr Glu Glu Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Glu Arg Glu Cys Val Glu Glu Thr Cys Ser Tyr Glu Glu Ala
1               5                   10                  15

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Asn Thr Phe Leu Glu Glu Val Arg Lys Gly Asn Leu Glu Arg Glu
1               5                   10                  15

Cys

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Ala Asn Thr Phe Leu Glu Glu Val Arg Lys Gly Asn Leu
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (6)..(7)
<223> OTHER INFORMATION: 4-carboxyglutamic acid

<400> SEQUENCE: 20

Cys Ala Asn Thr Phe Leu Glu Glu Val Arg Lys Gly Asn Leu
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Epsilon-aminocapronic acid
<220> FEATURE:
<221> NAME/KEY: misc_feature
<222> LOCATION: (6)..(11)
<223> OTHER INFORMATION: Disulfide bond between residues

<400> SEQUENCE: 21

Xaa Leu Glu Arg Glu Cys Val Glu Glu Thr Cys Ser Tyr Glu Glu Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Glu Arg Glu Cys Val Glu Glu Thr Cys Ser Tyr Glu Glu Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4-carboxyglutamic acid
<220> FEATURE:
<221> NAME/KEY: MOD_RES
<222> LOCATION: (4)..(4)
<223> OTHER INFORMATION: 4-carboxyglutamic acid
<220> FEATURE:
<221> NAME/KEY: MOD_RES
<222> LOCATION: (7)..(8)
<223> OTHER INFORMATION: 4-carboxyglutamic acid
<220> FEATURE:
<221> NAME/KEY: MOD_RES
<222> LOCATION: (13)..(14)
<223> OTHER INFORMATION: 4-carboxyglutamic acid

<400> SEQUENCE: 23

Leu Glu Arg Glu Cys Val Glu Glu Thr Cys Ser Tyr Glu Glu Ala
1               5                   10                  15

<210> SEQ ID NO 24
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(10)
<223> OTHER INFORMATION: Cyclic
<220> FEATURE:
<221> NAME/KEY: MOD_RES
<222> LOCATION: (14)..(14)
<223> OTHER INFORMATION: 4-carboxyglutamic acid

<400> SEQUENCE: 24

Leu Glu Arg Glu Cys Val Glu Glu Thr Cys Ser Tyr Glu Glu Ala
1               5                   10                  15
```

What is claimed is:

1. A method of detecting PIVKA-II antigen in a test sample, the method comprising the steps of: a) contacting the test sample with a monoclonal antibody having an antigen binding portion that binds to an epitope within amino acids 1-13 of PIVKA-II and for a time and under conditions sufficient for the formation of monoclonal antibody-antigen complexes; and b) detecting the presence of the monoclonal antibody-antigen complexes, wherein the presence of the monoclonal antibody-antigen complexes indicates the presence of PIVKA-II in the test sample, wherein the monoclonal antibody is a monoclonal antibody produced by a hybridoma cell line having ATCC deposit designation PTA-10541.

2. The method of claim 1, wherein the test sample is whole blood, serum or plasma.

3. The method of claim 1, wherein the monoclonal antibody is labeled with a detectable label and wherein (b) comprises measuring the signal generated by or emitted from the detectable label and detecting the PIVKA-II antigen in the test sample.

4. The method of claim 3, wherein the detectable label is selected from the group consisting of a radioactive label, an enzymatic label, a chemiluminescent label, a fluorescence label, a thermometric label, and an immuno-polymerase chain reaction label.

5. The method of claim 3, wherein the detectable label is an acridinium compound.

6. The method of claim 1, further comprising: a) generating or providing a source of hydrogen peroxide to the antibody-antigen complexes; b) adding a basic solution to the mixture of step (a); and c) measuring the light signal generated or emitted in step (b) and detecting PIVKA-II in the sample.

7. A method of detecting PIVKA-II antigen in a test sample comprising the steps of: a) contacting the test sample with a first monoclonal antibody having an antigen binding portion that binds to an epitope within amino acids 13-27 of PIVKA-II, for a time and under conditions sufficient for the formation of first monoclonal antibody-antigen complexes; b) adding a second monoclonal antibody to the first monoclonal antibody/antigen complexes, wherein the second monoclonal antibody has an antigen binding portion that binds to an epitope within amino acids 1-13 of PIVKA-II and is conjugated to a detectable label, for a time and under conditions sufficient to form first monoclonal antibody/antigen/second monoclonal antibody complexes; and c) measuring the signal generated by or emitted from the detectable label and detecting the PIVKA-II antigen in the test sample, wherein the second monoclonal antibody is a monoclonal antibody produced by a hybridoma cell line having ATCC deposit designation PTA-10541.

8. The method of claim 7, wherein the first monoclonal antibody is a monoclonal antibody produced by a hybridoma cell line having ATCC deposit designation PTA-9638.

9. The method of claim 7, wherein the test sample is whole blood, serum or plasma.

10. The method of claim 7, wherein the detectable label is selected from the group consisting of a radioactive label, an enzymatic label, a chemiluminescent label, a fluorescence label, a thermometric label, and an immuno-polymerase chain reaction label.

11. The method of claim 7, wherein the detectable label is an acridinium compound.

12. The method of claim 7, wherein the first monoclonal antibody is immobilized on a solid phase either before or after the formation of the first monoclonal antibody-antigen complexes.

13. A method of detecting PIVKA-II antigen in a test sample comprising the steps of: a) contacting the test sample with 1) a PIVKA-II reference antigen, wherein the reference antigen is attached to a detectable label capable of generating a detectable signal and 2) a monoclonal antibody to PIVKA-II antigen, for a time and under conditions sufficient to form PIVKA-II reference antigen/monoclonal antibody complexes; b) detecting a signal generated by the detectable label, wherein the amount of PIVKA-II antigen detected in the test sample is inversely proportional to the amount of PIVKA-II reference antigen bound to the monoclonal antibody, wherein the monoclonal antibody comprises an antigen-binding domain that binds to an epitope within amino acids 1-13 of PIVKA-II, wherein the monoclonal antibody is produced by a hybridoma cell line having ATCC deposit designation PTA-10541.

14. The method of claim 13, wherein the test sample is whole blood, serum or plasma.

15. The method of claim 13, wherein the detectable label is selected from the group consisting of a radioactive label, an enzymatic label, a chemiluminescent label, a fluorescence label, a thermometric label, and an immuno-polymerase chain reaction label.

16. The method of claim 13, wherein the detectable label is an acridinium compound.

17. A method for determining an amount of PIVKA-II in a sample comprising: a) contacting the test sample with at least two different binding proteins for a time and under conditions sufficient to form first binding protein/antigen/second binding protein complexes, wherein each binding protein comprises an antigen binding portion that specifically binds to a subset of amino acids 1-33 of PIVKA-II, wherein the antigen binding portion of each binding protein binds to a different subset of amino acids 1-33 of PIVKA-II, and wherein at least one of the binding proteins is conjugated to a detectable label; b) measuring the signal generated by or emitted from the detectable label; and c) determining the amount of PIVKA-II in the sample based on the signal, wherein the binding proteins are monoclonal antibodies, wherein a first monoclonal antibody has an antigen binding portion that binds to PIVKA-II, and a second monoclonal antibody has an antigen binding portion that binds to PIVKA-II and an antigen binding portion that binds to at least a subset of amino acids 1-33 of prothrombin, wherein the first monoclonal antibody has an antigen binding portion that binds to amino acids 13-27 of PIVKA-II, and the second monoclonal antibody has an antigen binding portion that binds to amino acids 1-13 of PIVKA-II, wherein the first monoclonal antibody is an antibody produced by the hybridoma cell line designated by American Type Culture Collection (ATCC) deposit designation PTA-9638, and the second monoclonal antibody is an antibody produced by the hybridoma cell line designated by American Type Culture Collection (ATCC) deposit PTA-10541.

* * * * *